United States Patent
Geach

(10) Patent No.: US 9,164,019 B2
(45) Date of Patent: Oct. 20, 2015

(54) SYSTEM AND METHOD FOR AUTOMATED DILUTION AND DELIVERY OF LIQUID SAMPLES TO AN OPTICAL PARTICLE COUNTER

(71) Applicant: CINRG SYSTEMS INC., Burlington (CA)

(72) Inventor: Alistair Geach, Burlington (CA)

(73) Assignee: CINRG Systems Inc., Burlington, Ontario (CA)

( * ) Notice: Subject to any disclaimer, the term of this patent is extended or adjusted under 35 U.S.C. 154(b) by 455 days.

(21) Appl. No.: 13/708,705

(22) Filed: Dec. 7, 2012

(65) Prior Publication Data

US 2014/0094969 A1   Apr. 3, 2014

(30) Foreign Application Priority Data

Sep. 27, 2012   (CA) .................................. 2791003

(51) Int. Cl.
| | |
|---|---|
| G05B 11/01 | (2006.01) |
| G01N 15/06 | (2006.01) |
| G01N 15/00 | (2006.01) |
| G01N 35/04 | (2006.01) |
| B01L 3/00 | (2006.01) |
| B01L 9/06 | (2006.01) |
| G01N 33/28 | (2006.01) |
| G01N 1/38 | (2006.01) |
| G01N 15/02 | (2006.01) |
| G01N 35/10 | (2006.01) |

(52) U.S. Cl.
CPC .............. *G01N 15/06* (2013.01); *B01L 3/5082* (2013.01); *B01L 9/06* (2013.01); *G01N 1/38* (2013.01); *G01N 15/00* (2013.01); *G01N 15/0205* (2013.01); *G01N 33/2888* (2013.01); *G01N 35/04* (2013.01); *G01N 35/1095* (2013.01); *G05B 11/01* (2013.01); *G01N 2015/0693* (2013.01); *G01N 2035/0491* (2013.01)

(58) Field of Classification Search
CPC ... G05B 11/01; G01N 33/2888; G01N 15/00; G01N 35/04; G01N 2035/0491; G01N 15/06; G01N 15/0205; G01N 35/1095; G01N 1/38; G01N 2015/0693; B01L 3/5082; B01L 9/06
USPC ......................................................... 700/265
See application file for complete search history.

(56) References Cited

U.S. PATENT DOCUMENTS

| | | | | | |
|---|---|---|---|---|---|
| 3,772,154 | A | * | 11/1973 | Isenberg et al. ................. | 435/33 |
| 5,806,282 | A | * | 9/1998 | Hansen ........................... | 53/432 |
| 6,436,349 | B1 | * | 8/2002 | Carey et al. .................... | 422/64 |
| 6,829,954 | B2 | * | 12/2004 | Katagi ....................... | 73/864.25 |

(Continued)

*Primary Examiner* — Charles Kasenge
(74) *Attorney, Agent, or Firm* — Patrick J. Hofbauer

(57) ABSTRACT

A system for the automated dilution and delivery of mixtures of diluent and liquid samples to a particle counter comprises a container positioning member for receiving and retaining congruent sample containers with a volume of liquid sample therein. An automated diluent pumping mechanism draws a respective volume of a diluent from a diluent source and introduces the diluent into the each sample container for mixing with the unknown volume of liquid sample within each sample container to together form a mixture that is substantially equal to a pre-determined threshold volume. A mixer agitates the mixture in the sample containers. An automated mixture pumping mechanism sequentially draws a respective volume of mixture from the sample containers and delivers the drawn volume of the mixture to the optical particle counter for testing.

36 Claims, 18 Drawing Sheets

(56) References Cited

U.S. PATENT DOCUMENTS

| | | | |
|---|---|---|---|
| 7,360,984 B1 * | 4/2008 | Sugiyama et al. | 414/798.1 |
| 7,488,451 B2 * | 2/2009 | Zarowitz et al. | 422/67 |
| 7,718,072 B2 * | 5/2010 | Safar et al. | 210/695 |
| 7,752,892 B2 * | 7/2010 | Muller et al. | 73/49.2 |
| 8,083,995 B2 * | 12/2011 | Tsutsumida et al. | 422/65 |
| 8,211,301 B2 * | 7/2012 | Safar et al. | 210/222 |
| 8,357,538 B2 * | 1/2013 | Self et al. | 436/47 |
| 8,507,279 B2 * | 8/2013 | Ball et al. | 436/10 |
| 8,703,492 B2 * | 4/2014 | Self et al. | 436/47 |
| 8,728,311 B2 * | 5/2014 | Safar et al. | 210/222 |
| 2003/0064393 A1 * | 4/2003 | Bass et al. | 435/6 |
| 2003/0213313 A1 * | 11/2003 | Katagi | 73/864.25 |
| 2005/0084423 A1 * | 4/2005 | Zarowitz et al. | 422/100 |
| 2008/0015116 A1 * | 1/2008 | Bass et al. | 506/35 |
| 2008/0206098 A1 * | 8/2008 | Tsutsumida et al. | 422/67 |
| 2010/0128555 A1 * | 5/2010 | Hughes | 366/132 |
| 2011/0008816 A1 * | 1/2011 | Ball et al. | 435/29 |

* cited by examiner

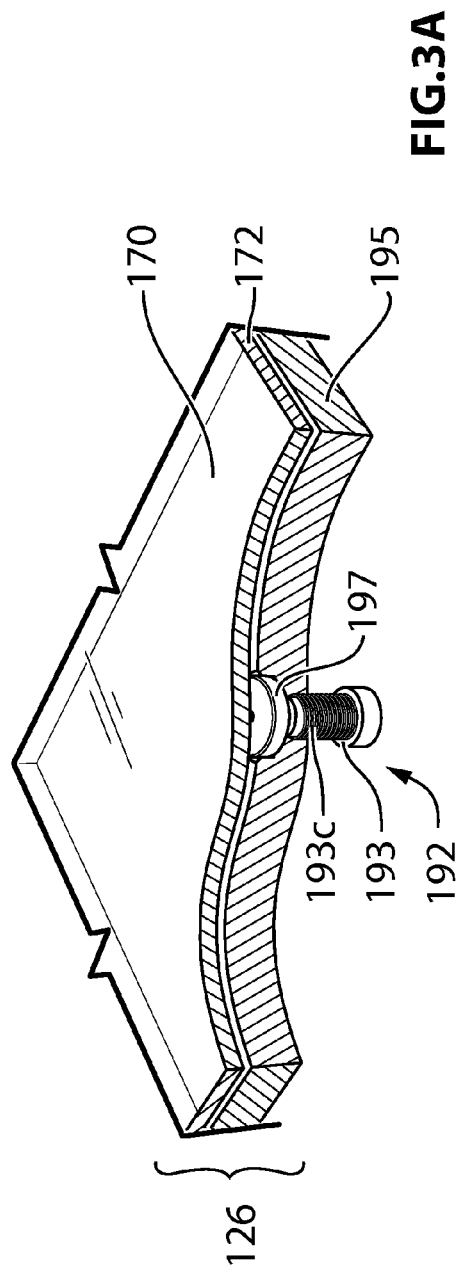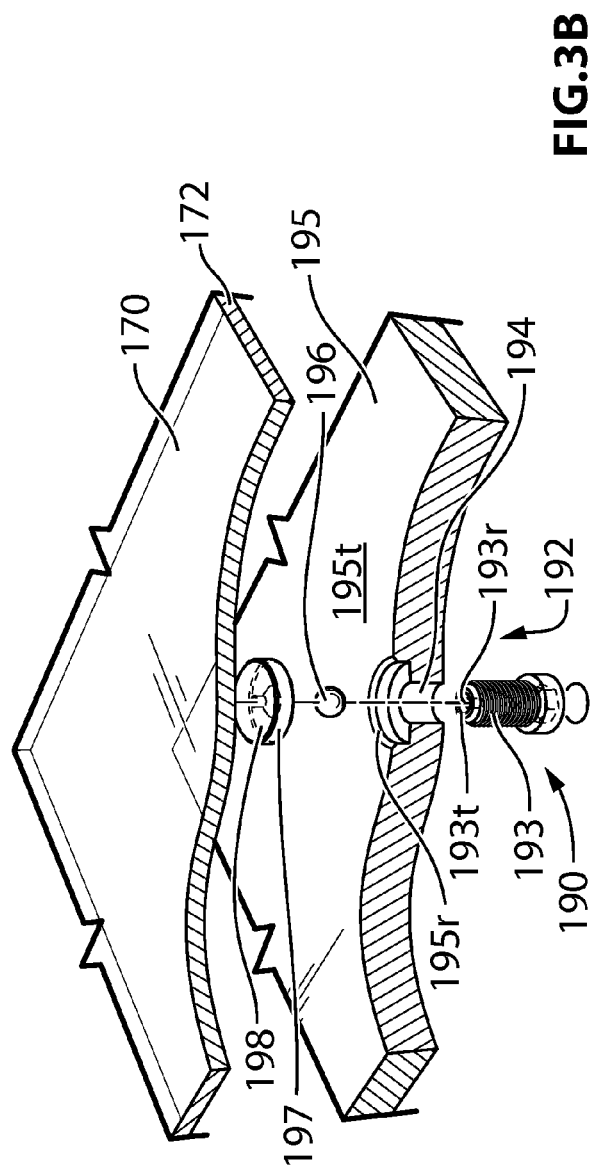

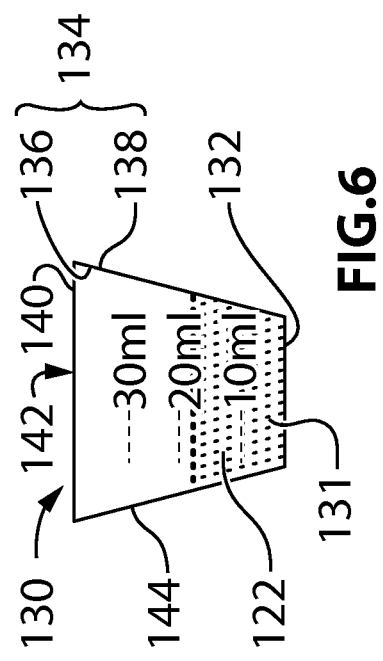
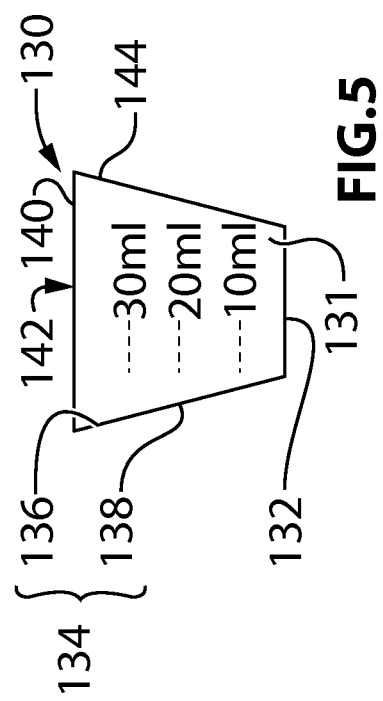

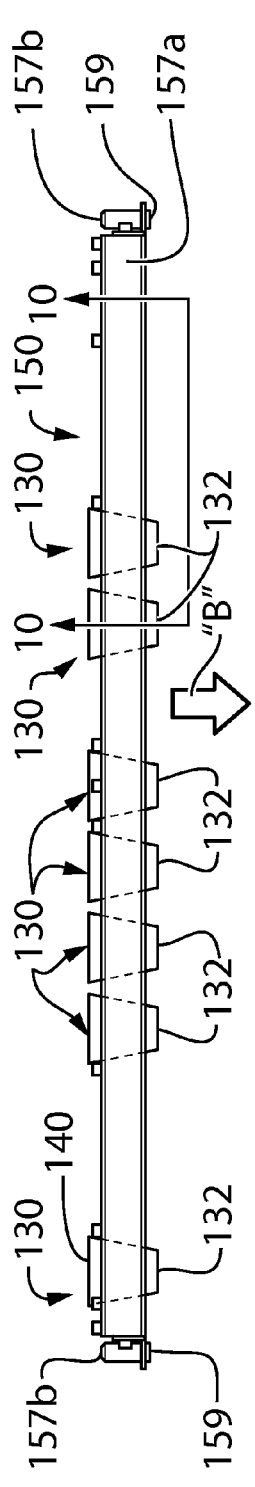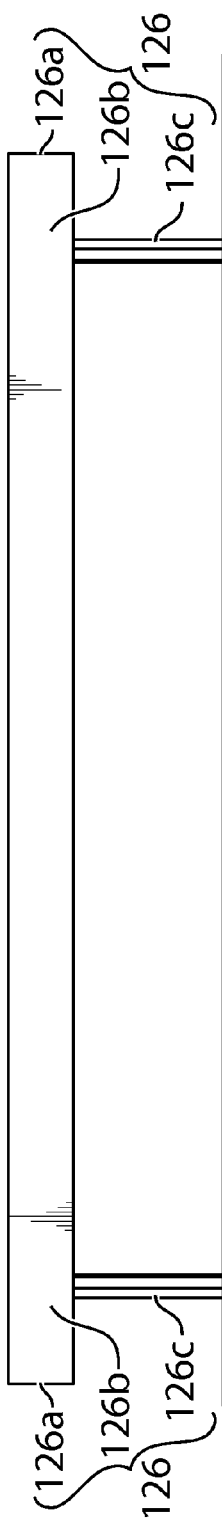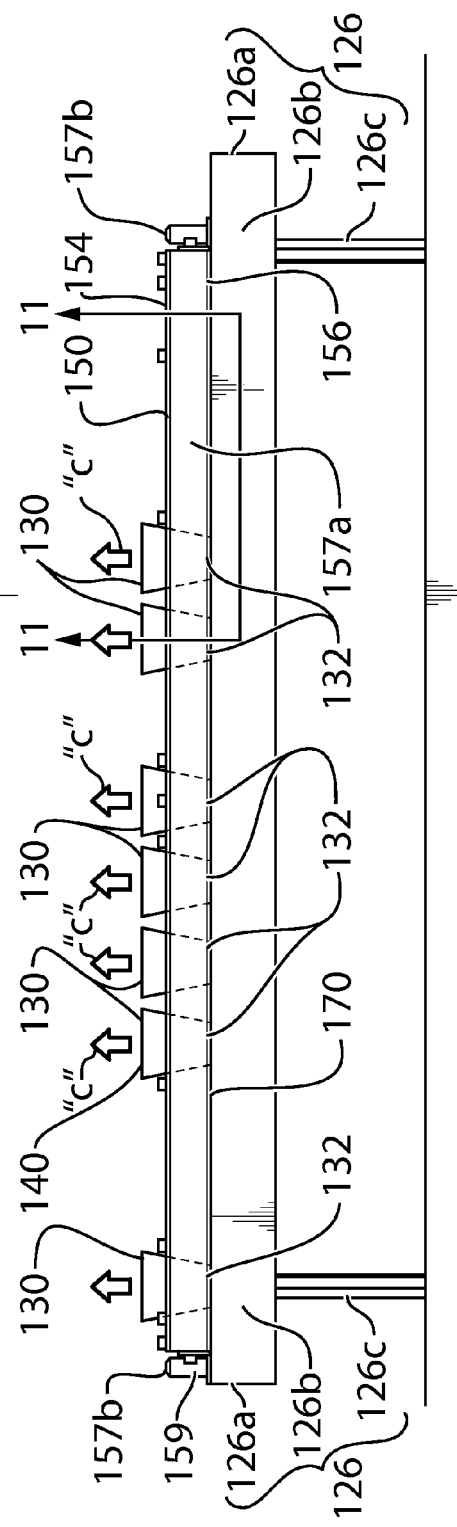
FIG.8
FIG.9

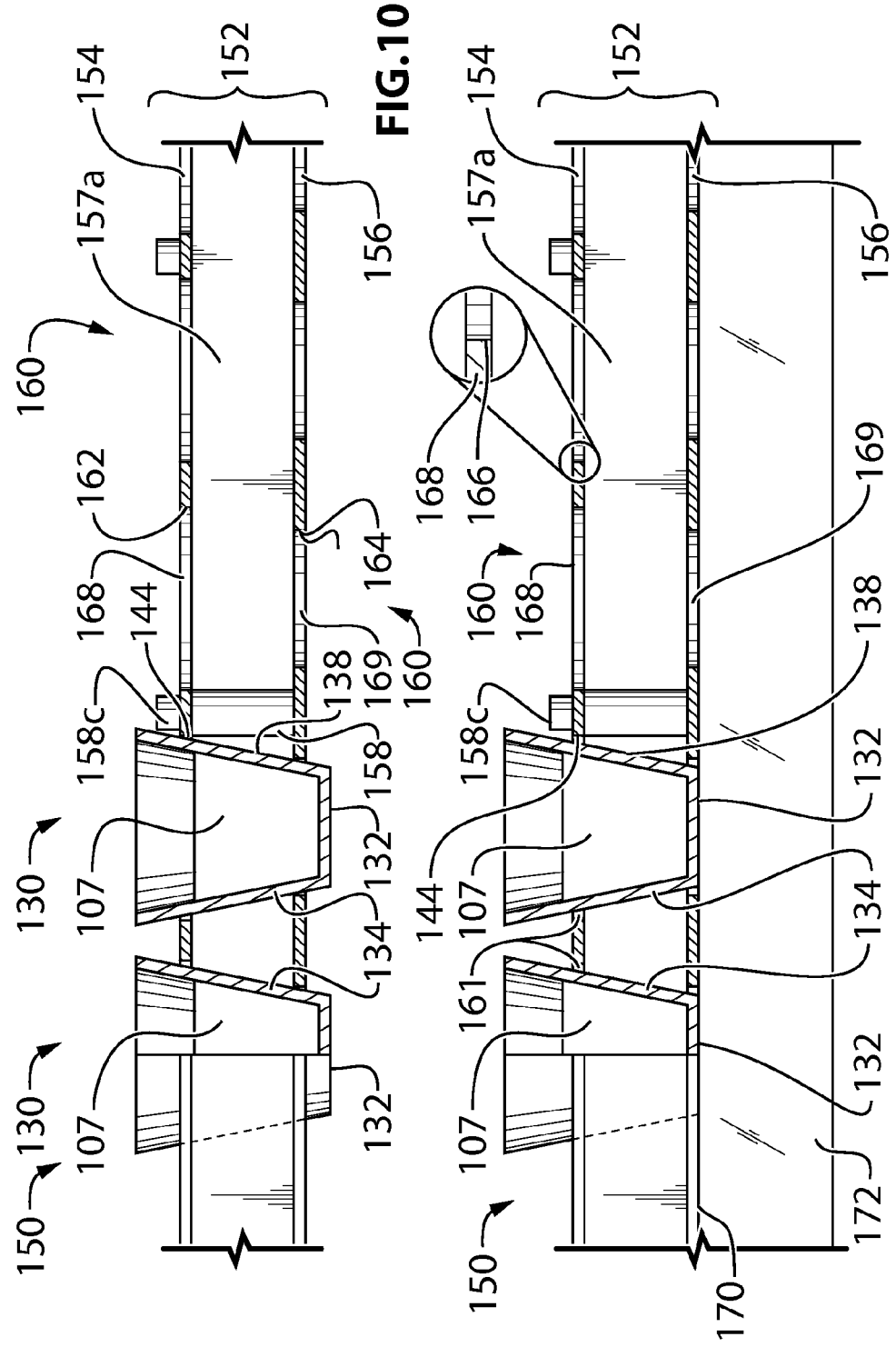

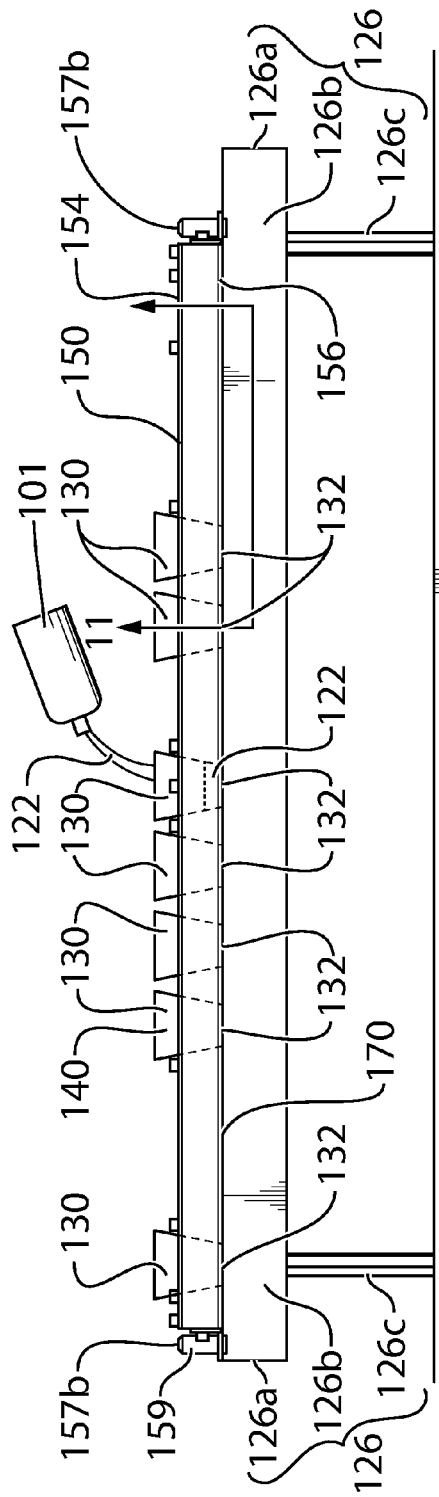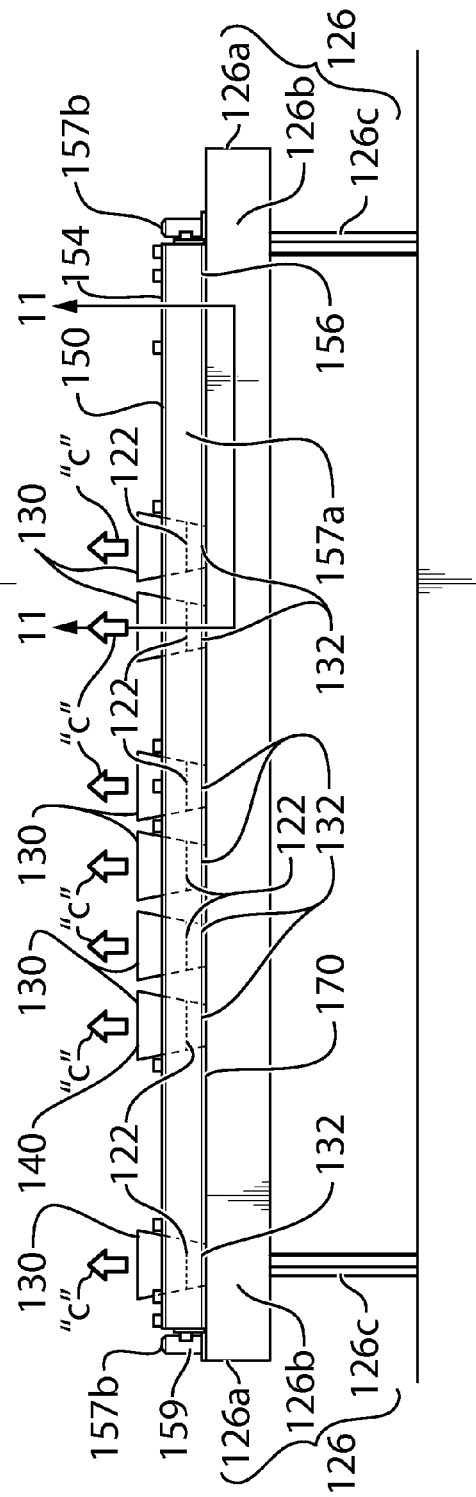

SYSTEM AND METHOD FOR AUTOMATED DILUTION AND DELIVERY OF LIQUID SAMPLES TO AN OPTICAL PARTICLE COUNTER

FIELD OF THE INVENTION

The present invention relates generally to equipment and methods used with optical particle counters for determining the size and concentration of particles of different sizes contained with liquid samples, and more particularly to a system and method for the automated dilution and delivery of a plurality of liquid samples in a batch process to such optical particle counters.

BACKGROUND OF THE INVENTION

It is common to quantitatively measure the size and concentration of particulate contaminates in liquids, such as new and used oils, in order to determine various characteristics of the liquids. In samples of used oil, for instance, there are both "hard particles" that are targeted for measurement in terms of size and concentration, and similarly-sized "soft particles" that inhibit the accurate measurement of the hard particles. The presence of soft particles in a liquid sample is known to significantly elevate particle counts to the point where their presence compromises the validity of the count data obtained. It has been found, however, that the addition of a suitable diluent to oil samples, can substantially eliminate the interference of soft practices in obtaining accurate hard particle count data.

Hard particles in oil include without limitation, dirt and metal fragments, which have a serious impact on the life of equipment by accelerating wear and erosion. Such hard particles originate from a variety of sources, including generation from within an operating fluid system, ingress into the operating fluid system, or contamination that may occur during the storage and handling of new oils. Typically, "soft particles" include certain additives or additive by-products that are semi-insoluble or insoluble in oil, and other similar materials that are not known to directly increase wear and erosion within an operating system, such as, for example, air bubbles and water bubbles.

The measurement of such contaminants is particularly important in order to identify the potential problems with samples of new or used oils, to determine the characteristics of various types of new or used oils, and also to determine whether engines and/or machinery are introducing metal particles into used oil. More particularly, particle count results can be used to aid in assessing the capability of the filtration system responsible for cleaning oil or other fluid, determining if off-line recirculating filtration is needed to clean up the fluid system, or aiding in the decision of whether or not a fluid change is required. An abnormal particle count may trigger concerns of these possibilities, which can be confirmed by additional testing.

Fundamentally, in order to permit the calculation of useful and relevant data related to particles found in fluids, such as oil, the quantity of various sizes of contaminants needs to be determined. It is well known that in order to be useful, such measurement requires quantitative guidelines in order to meaningfully present the results. Accordingly, various standards are used for testing and reporting fluid cleanliness. Two such standards include the SAE Aerospace Standard (AS) and the ISO Code System. It has been found useful to group particle sizes into coded ranges in order to permit ready handling and manipulation of the data. The following table illustrates one such standard of measurement as per the SAE Aerospace Standard (AS) system, with the codes for each range given in the left-most column.

| | Cleanliness Classes for Differential Particle Counts (particles/100 ml) | | | | |
| --- | --- | --- | --- | --- | --- |
| | Size | | | | |
| Code | 6 μm (c) to 14 μm(c) | 14 μm(c) to 21 μm(c) | 21 μm(c) to 38 μm(c) | 38 μm(c) to 70 μm(c) | >70 μm(c) |
| 00 | 126 | 22 | 4 | 1 | 0 |
| 0 | 250 | 44 | 8 | 2 | 0 |
| 1 | 500 | 89 | 16 | 3 | 1 |
| 2 | 1000 | 178 | 32 | 6 | 1 |
| 3 | 2000 | 356 | 63 | 11 | 2 |
| 4 | 4000 | 712 | 126 | 22 | 4 |
| 5 | 8000 | 1425 | 253 | 45 | 8 |
| 6 | 16000 | 2850 | 506 | 90 | 16 |
| 7 | 32000 | 5700 | 1012 | 180 | 32 |
| 8 | 64000 | 11400 | 2025 | 360 | 64 |
| 9 | 128000 | 22800 | 4050 | 720 | 128 |
| 10 | 256000 | 45600 | 8100 | 1440 | 256 |
| 11 | 512000 | 91200 | 16200 | 2880 | 512 |
| 12 | 1024000 | 182400 | 32400 | 5760 | 1024 |

It is well known to use automated optical particle counters to quantitatively measure the size and concentration of particulate contaminants in samples of fluids, such as new and used oil. Commonly, such optical particle counters perform analysis based on the light extinction principle, using a laser beam passing through a liquid sample. Such optical particle counters are capable of recording the size and number of particles as they pass across a detector, and such equipment typically includes a sampling apparatus that automatically delivers a pre-determined volume of liquid specimen at a controlled flow rate to the optical sensing cell of the optical particle counter. Examples of prior art optical particle counters are taught in, amongst others, U.S. Pat. No. 5,426,501 (Hokanson et al.) issued Jun. 20, 1995, and U.S. Pat. No. 5,172,004 (Furuya) issued Dec. 15, 1992. Indeed, tests performed by such automated optical particle counters are considered by many to be the single most important test for oil analysis.

There are various well-known problems associated with the use of optical particle counters to test liquid samples, especially samples of oil. One of the two most fundamental problems is that of particle co-incidence. Particle co-incidence occurs when more than one particle is present in the optical sensing cell of the optical particle counter at the same time and a "large" particle is falsely detected rather than two (or more) smaller ones. It is well known that particle co-incidence causes inaccurate counting of the "hard particles" due to the presence of other type of particles, such as the "soft particles" in the liquid sample. Soft particles cause false high counts of particles in their size category, thus yielding false counts and an over-estimation of contamination levels across all sizes. Dilution of samples with a suitable diluent can reduce the probability of particle co-incidence.

Particle co-incidence can also occur due to the existence of air bubbles in the oil, thereby causing false positive readings. Bubbles can be caused by overly vigorous mixing or agitation of a liquid sample, which mixing may be necessary as part of the test procedure. Further, suspended or free water in the oil will generally be counted as particles.

Another fundamental problem associated with the use of optical particle counters to test liquid samples is that of the proper flow of high viscosity liquid samples. The forces required in order to develop the necessary pressure to rapidly achieve the required flow rate of the liquid samples through the optical sensing cell becomes quite significant, and even prohibitive. For this reason, it is extremely difficult to properly and accurately test high viscosity liquid samples in an optical particle counter without sample dilution using a suitable diluent.

In spite of the above stated advantages of using diluted oil samples for testing with optical particle counters, the vast majority of such testing is still carried out on undiluted samples where the oil sample to be tested is taken directly from a sample bottle without dilution. In such cases, a mechanically controlled syringe is typically used to draw up a measured volume of the liquid sample and inject it directly into the inlet port of the optical sensing cell of the optical particle counter. Alternatively, a sampling tube connected to the optical sensing cell inlet is lowered into the sample bottle. Pressure is used to force the liquid sample through the optical sensing cell of the optical particle counter. Samples are typically processed one by one (i.e., not in a batch process), with the optical sensing cell and feeding tubes being cleaned with solvent between tested samples.

Where liquid sample to be tested by optical particle counting are to be diluted prior to such testing in the prior art, it is common to manually measure and mix known quantities of the liquid sample and of a suitable diluent prior to testing. More specifically, a laboratory pipette is often used to manually draw a quantity of liquid from each sample bottle, as measured against volume markings on the pipette, and to inject this drawn quantity of liquid sample from the pipette into a sample container. This process is then repeated by pipette for adding a measured volume of a suitable diluent to the sample container. The two volumes are then summed for purposes of use in any subsequent calculations required to convert raw particle counts taken from a sample into standardized volumetric particle counts.

Although manual pipetting is accurate, it has a number of significant drawbacks associated with it, particularly where carried out repetitively for a high number of liquid samples to be subsequently presented for testing by an optical particle counter. These problems include, without limitation: i) pipetting is labour intensive (i.e., time consuming) for the operator carrying out the procedure; ii) pipetting is tedious for the operator carrying out the procedure; iii) the preparation of test samples cannot be performed outside of normal laboratory operation hours without special (and typically more expensive) arrangements being made to staff the test facility with appropriate laboratory personnel; and, iv) operators carrying out the pipetting procedure for large numbers of test samples are susceptible to repetitive strain injuries.

In order to improve and standardize methods for optical particle counting utilizing diluted liquid samples, ASTM International of West Conshohocken, Pa., USA has developed and published a test protocol known as ASTM-D7647 and entitled "Test Method for Automatic Particle Counting of Lubricating and Hydraulic Fluids Using Dilution Techniques to Eliminate the Contribution of Water and Interfering Soft Particles by Light Extinction". ASTM-D7647 prescribes a standardized testing methodology that requires the use of a diluent to dilute the original samples to specified ratios of oil to diluent, prior to optical particle counting readings taking place. It has been found that the ASTM-D7647 test protocol notably addresses the particle count inaccuracy issues caused by particle coincidence and soft particles (as discussed above), especially where high viscosity liquids are being tested. Accordingly, the erroneous contribution of soft particles to the particle size cumulative count is substantially negated by the ASTM-D7647 methodology. The quality of particle count data is significantly improved on many samples as the effects of known interference are removed. The present invention discloses and claims, in its simplest non-limiting terms, a system for the automatic dilution and delivery of a plurality of liquid test samples to an optical particle counter for batch testing of diluted liquid samples according to ASTM-D7647 in a more accurate and efficient manner than has been possible with prior art sample handling equipment and methodologies.

In spite of the fact that ASTM-D7647 test protocol provides significantly more accurate automated optical particle counts than earlier testing methods, it has not gained widespread commercial acceptance. This lack of widespread commercial acceptance is thought in large part to stem from the fact that while the injection of the test sample into the optical sensing cell and the reading of particle counts by the optical sensing cell may be substantially automated through the use of existing equipment, the preparation and presentation of the test samples, including the addition of the aforesaid diluent (by prior art manual pipetting techniques), has not been significantly automated to date, and remains extremely labour intensive. In other words, the testing of diluted oil samples using the ASTM-D7647 protocol is presently known to be used only with manual sample presentation procedures, which include pipetting, as aforesaid, with all of the attendant problems and difficulties previously mentioned. As such, while ASTM-D7647 is able to obtain improved particle count results over earlier testing methodologies which do not involve the addition of a diluent to the original sample volume to be tested, the prior art drawbacks associated with pipetting, represent an ongoing limitation to its widespread commercial acceptance, particularly in light of the fact that the number of pipetting operations per sample tested has necessarily been doubled over prior methodologies not utilizing sample dilution.

Apart from manual pipetting of samples and diluent as discussed above, there is presently no known apparatus, system, or method for reliably automating the dilution and delivery of liquid samples of oils and hydraulic fluids to an optical particle counter, in accordance with the ASTM-D7647 test protocol.

It is therefore an object of the present invention to provide an improved system for reliably automating the dilution and delivery of a plurality of mixtures of diluent and liquid samples respectively disposed in an equal plurality of congruent sample containers to an optical particle counter in compliance with the ASTM-D7647 testing protocol.

It is a further object of the present invention to provide an improved system for reliably automating the dilution and delivery of a plurality of mixtures of diluent and liquid samples respectively disposed in an equal plurality of congruent sample containers to an optical particle counter in a manner that eliminates the need for manual pipetting of the liquid samples or of any diluents added to such liquid samples before such testing.

It is a further object of the present invention to provide an improved system for reliably automating the dilution and delivery of a plurality of mixtures of diluent and liquid samples respectively disposed in an equal plurality of congruent sample containers to an optical particle counter, wherein presentation of such mixtures for automated testing is less labour-intensive than with known prior art equipment and methods used for this purpose.

It is yet another object of the present invention to provide an improved system for reliably automating the dilution and delivery of a plurality of mixtures of diluent and liquid samples respectively disposed in an equal plurality of congruent sample containers to an optical particle counter, wherein The system permits for much more prompt and uniform presentation of such mixtures for testing on a batch process basis.

It is still an object of the present invention to provide an improved system for reliably automating the dilution and delivery of a plurality of mixtures of diluent and liquid samples respectively disposed in an equal plurality of congruent sample containers to an optical particle counter, wherein The system precludes the operator performing the preparation of such mixtures from becoming unduly fatigued or from incurring repetitive strain injuries.

It is also an object of the present invention to provide an improved system for reliably automating the dilution and delivery of a plurality of mixtures of diluent and liquid samples respectively disposed in an equal plurality of congruent sample containers to an optical particle counter, wherein The system permits comparable testing accuracy to prior art manual dilution methods that use a pipette.

It is yet another object of the present invention to provide an improved system for reliably automating the dilution and delivery of a plurality of mixtures of diluent and liquid samples respectively disposed in an equal plurality of congruent sample containers to an optical particle counter, which apparatus permits an accurate automated determination of the volume of the liquid sample and of any diluent required to be added to said sample in order to provide for automated filling of each said test container to a standard test volume prior to commencement of said automated testing.

It is yet another object of the present invention to provide an improved system for reliably automating the dilution and delivery of a plurality of mixtures of diluent and liquid samples respectively disposed in an equal plurality of congruent sample containers to an optical particle counter, which apparatus permits automated dilution of the liquid samples to be tested, especially new and used oils, in the higher viscosity ranges.

It is yet another object of the present invention to provide an improved system for reliably automating the dilution and delivery of a plurality of mixtures of diluent and liquid samples respectively disposed in an equal plurality of congruent sample containers to an optical particle counter, the construction of which apparatus is relatively simple, compact, and economical.

It is yet another object of the present invention to provide an improved system for reliably automating the dilution and delivery of a plurality of mixtures of diluent and liquid samples respectively disposed in an equal plurality of congruent sample containers to an optical particle counter, which system saves the time and expense of manual sample presentation methods which make uses of pipetting, and which presents the mixtures in an ordered array, so as to allow automated testing of the presented liquid samples without the need for additional manual manipulation or supervision of the mixtures during said automated testing, thereby permitting such testing to run outside of normal laboratory operational hours.

It is yet another object of the present invention to provide an improved system for reliably automating the dilution and delivery of a plurality of mixtures of diluent and liquid samples respectively disposed in an equal plurality of congruent sample containers to an optical particle counter, which system maximizes the effective capacity of operators by freeing them from the need for manual pipetting of liquid samples.

It is yet another object of the present invention to provide an improved system for reliably automating the dilution and delivery of a plurality of mixtures of diluent and liquid samples respectively disposed in an equal plurality of congruent sample containers to an optical particle counter, which apparatus precludes operators from experiencing repetitive strain injuries by reason of the elimination of pipetting tasks associated with such presentation in the prior art.

It is yet another object of the present invention to provide an improved system for reliably automating the dilution and delivery of a plurality of mixtures of diluent and liquid samples respectively disposed in an equal plurality of congruent sample containers to an optical particle counter, which system permits the dilution and delivery of a plurality of mixtures of diluent and liquid samples contained in congruent sample containers to an optical particle counter, in accordance with the ASTM-D7647 test protocol.

It is yet another object of the present invention to provide an improved system for reliably automating the dilution and delivery of a plurality of mixtures of diluent and liquid samples respectively disposed in an equal plurality of congruent sample containers to an optical particle counter, which system facilitates and promotes the adoption of the ASTM-D7647 test method on a more widespread commercial scale.

SUMMARY OF THE INVENTION

In accordance with one aspect of the present invention there is disclosed herein a novel system for the automated dilution and delivery of a plurality of mixtures of diluent and liquid samples respectively disposed in an equal plurality of congruent sample containers to an optical particle counter, the congruent sample containers having an upwardly facing open mouth. The system comprises a container positioning member for receiving and retaining the congruent sample containers in an array with a respective unknown volume of liquid sample having been poured into each sample container, wherein the unknown volume of each liquid sample is less than a pre-determined threshold volume that is less than the total volume of the respective sample container. An automated diluent pumping mechanism, having a diluent ingress port in fluid communication with a diluent source and a diluent egress port, is positionable in programmed sequence over the open mouth of each of the congruent sample containers retained in the array, so as to be able to draw a respective volume of a suitable diluent from the diluent source and to introduce the drawn volume of the diluent though the open mouth of each sample container for mixing with the respective unknown volume of the liquid sample already placed within each sample container, to together form a mixture of the liquid sample and diluent, wherein the volume of the mixture is substantially equal to the pre-determined threshold volume. There is also provided a mixer for agitating the mixture of liquid sample and diluent in the sample containers. Further, an automated mixture pumping mechanism is provided, with said mechanism having a mixture ingress port positionable in the programmed sequence over the mouth of each of the congruent sample containers retained in the array, so as to be in fluid communication with the mixture of liquid sample and diluent in each sample container, and a mixture egress port in fluid communication with the optical particle counter, for sequentially drawing a respective volume of mixture of diluent and liquid sample from the sample containers and for delivering the respective drawn volume of mixture of the liquid sample and the diluent to the optical particle counter.

In accordance with another aspect of the present invention, the system further comprises an ultrasonic measuring device having an ultrasonic transducer and an ultrasonic sensor, for measuring the vertical position of the top surface of the liquid sample in each selected sample container with respect to said ultrasonic measuring device.

In accordance with a further aspect of the present invention, the system further comprises a computer/CPU that is connected in data communicating relation to said ultrasonic measuring device and that is programmed to calculate an accurate height measurement of the top surface of the liquid sample in the selected sample container with respect to an upwardly directed planar reference surface, using the measurement of the vertical position of the top surface of the liquid sample.

In accordance with a still further aspect of the present invention there is disclosed herein a method of automatic dilution and delivery of a plurality of mixtures of diluent and liquid samples respectively disposed in an equal plurality of congruent sample containers to an optical particle counter, the congruent sample containers having an upwardly facing open mouth, the method comprising the steps of: (a) receiving and retaining a plurality of congruent sample containers in an array in a container positioning member on a upwardly directed planar reference surface; (b) placing an unknown volume of the liquid sample into each sample container, wherein the unknown volume of each liquid sample is less than a pre-determined threshold volume that is less than the total volume of the respective sample container; (c) drawing a respective volume of a suitable diluent from a diluent source; (d) introducing the drawn volume of the diluent though the open mouth of each sample container for mixing with the respective unknown volume of the liquid sample placed within each sample container to together form a mixture of the liquid sample and diluent, wherein the volume of the mixture is substantially equal to the pre-determined threshold volume; (e) agitating the mixture of liquid sample and diluent in the sample containers; and, (f) sequentially drawing a respective volume of mixture of liquid sample and diluent from the sample containers; and (g) delivering the respective drawn volume of mixture of the liquid sample and the diluent to the optical particle counter.

In accordance with another aspect of the present invention, the method further comprises the step of, after step (b), above, but before step(c), above:
- (b2) mechanically moving a measurement mechanism into place over said unknown volume of liquid in said selected sample container; and,
- (b3) electronically measuring the vertical position of the top surface of the liquid sample in each selected sample container with respect to said measurement device.

These and other objects, advantages, features and characteristics of the present invention, as well as methods of operation and functions of the related elements of the structure and method, together with the combination of parts and economies of manufacture and process, will become more apparent upon consideration of the following detailed description and the appended claims with reference to the accompanying drawings, the latter of which is briefly described herein below.

BRIEF DESCRIPTION OF THE DRAWINGS

The novel features which are believed to be characteristic of the method and apparatus for dilution and delivery of a plurality of mixtures of diluent and liquid samples respectively disposed in an equal plurality of congruent sample containers to an optical particle counter according to the present invention, as to its structure, organization, use and method of operation, together with further objectives and advantages thereof, will be better understood from the following drawings in which a presently preferred embodiment of the invention will now be illustrated by way of example. It is expressly understood, however, that the drawings are for the purpose of illustration and description only, and are not intended as a definition of the limits of the invention. In the accompanying drawings:

FIG. 3A is a cut-away perspective view of a portion of the base member of FIG. 2, showing one of the gimbal mounts there beneath;

FIG. 3B is an exploded cut-away perspective view of FIG. 3A;

FIG. 5 is an enlarged side elevational view of an empty sample container;

FIG. 6 is an enlarged side elevational view of the sample container of FIG. 5, but with a volume of liquid sample therein;

FIG. 8 is a front elevational view of The system shown in FIG. 1, with the container positioning member being removed from its in-use sampling configuration;

FIG. 9 is a front elevational view similar to FIG. 8, but with the container positioning member shown in its in-use sampling configuration;

FIG. 10 is a sectional front elevational view taken along section line 10-10 of FIG. 8;

FIG. 11 is a sectional front elevational view taken along section line 11-11 of FIG. 9;

FIG. 16 is a front elevational view similar to FIG. 9, showing an unknown volume of liquid sample being poured into each congruent sample container;

FIG. 17 is a front elevational view similar to FIG. 16, showing a pre-determined threshold volume of a mixture of liquid sample and diluent being the same volume for each sample container;

DETAILED DESCRIPTION OF THE PREFERRED EMBODIMENT

Figure 1:
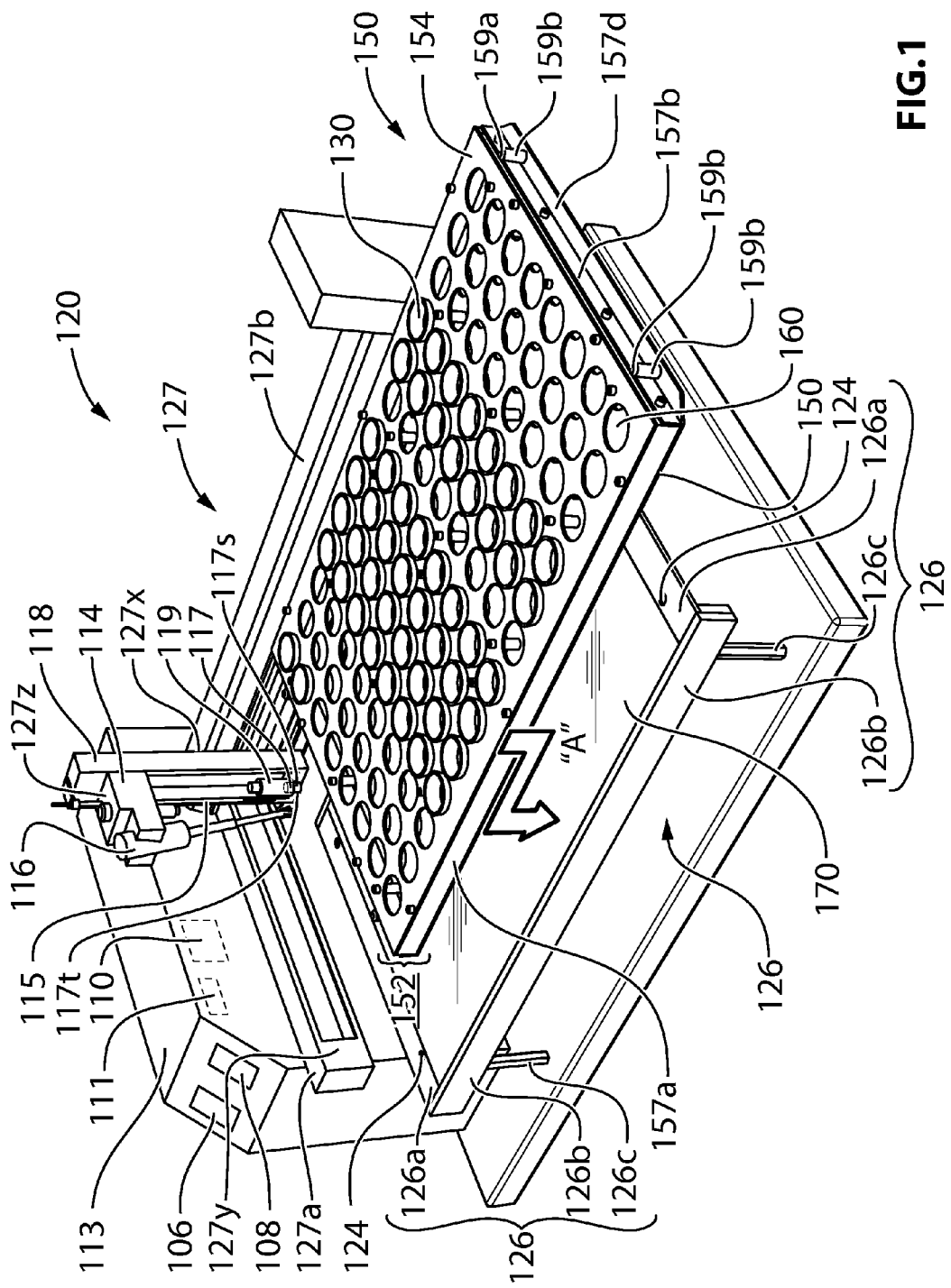
FIG. 1 is a perspective view illustrating an embodiment of a system according to the invention shown in use with an optical particle counter and with the container positioning member removed from its in-use sampling configuration.
Figure 2:
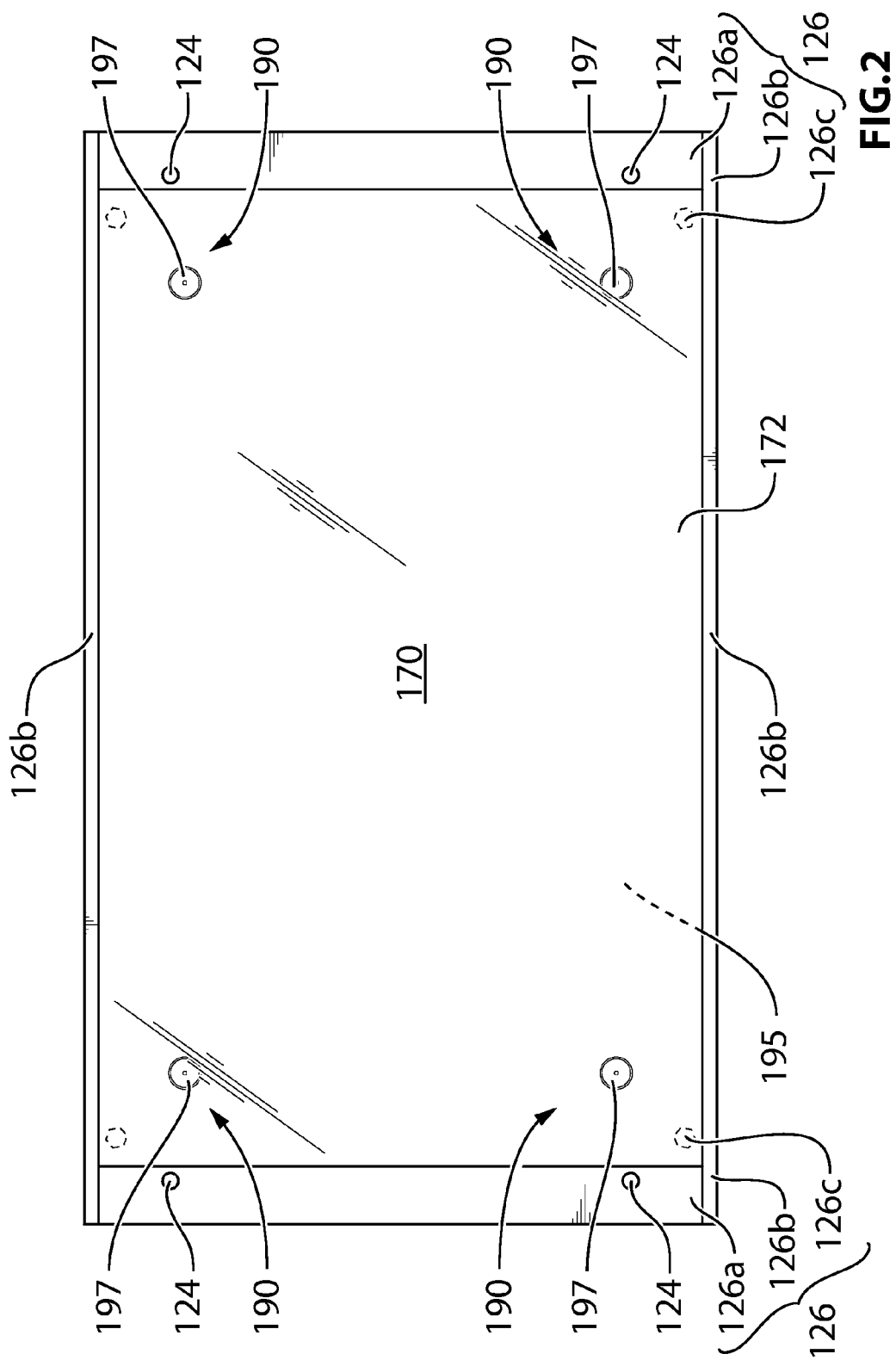
FIG. 2 is a top plan view of the base member of The system of FIG. 1, with the container positioning member completely removed from view.
Figure 4:
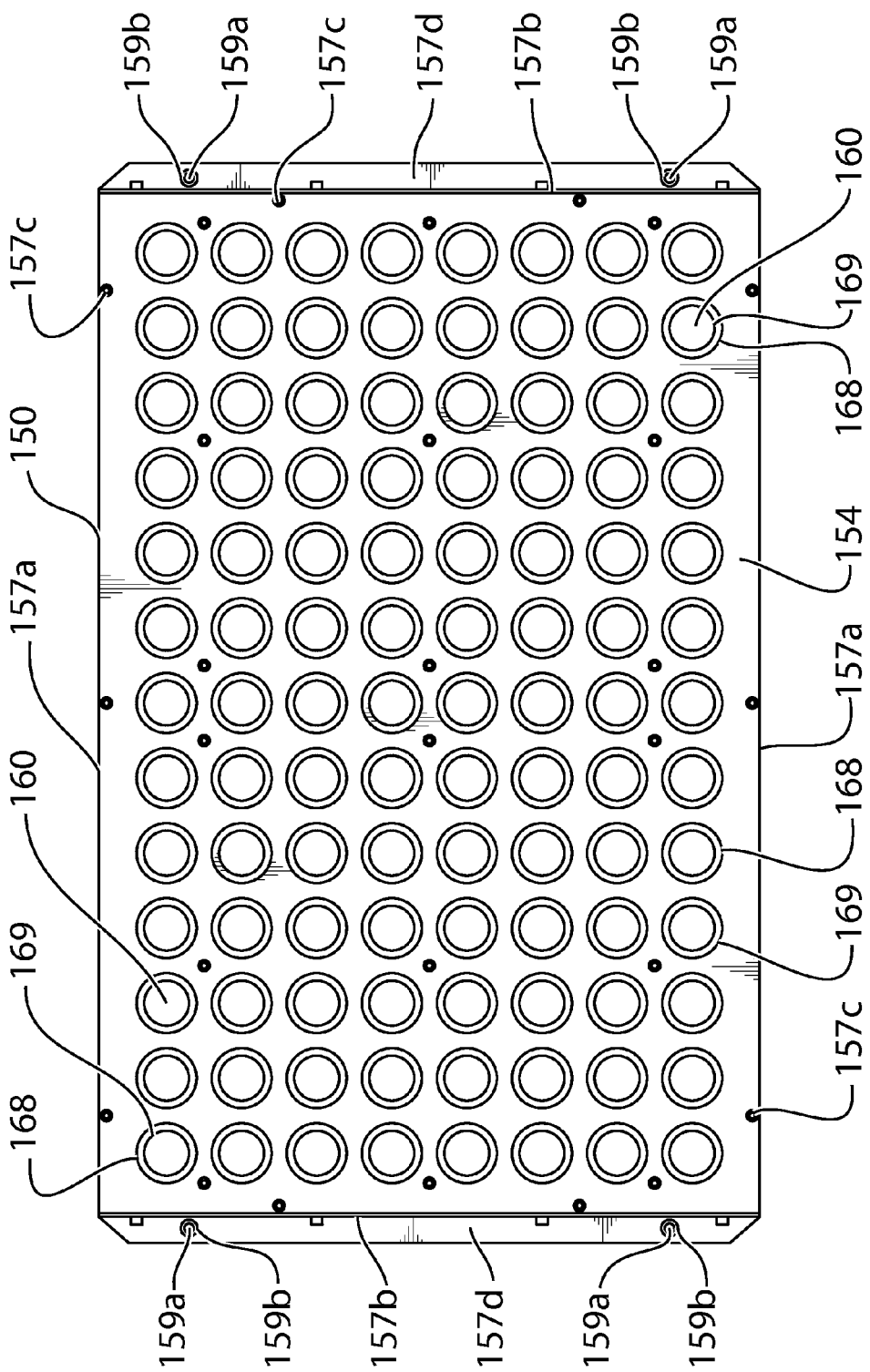
FIG. 4 is a top plan view of the container positioning member of FIG. 1, with all of the congruent sample containers removed therefrom.

Reference will now be made to FIGS. 1 through 22, which show an exemplary embodiment of a system, as indicated by the general reference numeral 120, according to the present invention, for the automated dilution and delivery of a plurality of mixtures 107 of diluent 103 and liquid samples 122 respectively disposed in an equal plurality of congruent sample containers 130 to an optical particle counter, as indicated by the general reference numeral 110. In overview, the system 120 claimed herein comprises, in broad, non-limiting terms, four main components, namely a container positioning member 150, an automated diluent pumping mechanism 108, an automated mixer 116, and an automated mixture pumping mechanism 106, as will be described in more detail below.

The container positioning member 150 is manually movable by an operator from an operative in-use sampling configuration (see FIGS. 9 and 11) wherein it rests atop the base member 126 with the base 132 of each one of a plurality of congruent sample containers 130 resting on an upwardly directed reference surface 170, to a plurality of configurations (see for example FIGS. 1 and 8) wherein the container positioning member 150 is removed from such resting contact with the reference surface 170, as will be described below in considerably more detail. In the operative in-use sampling configuration, the congruent sample containers 130 are retained in an array for sequential access by the system 120, as described more fully below.

Figure 13:
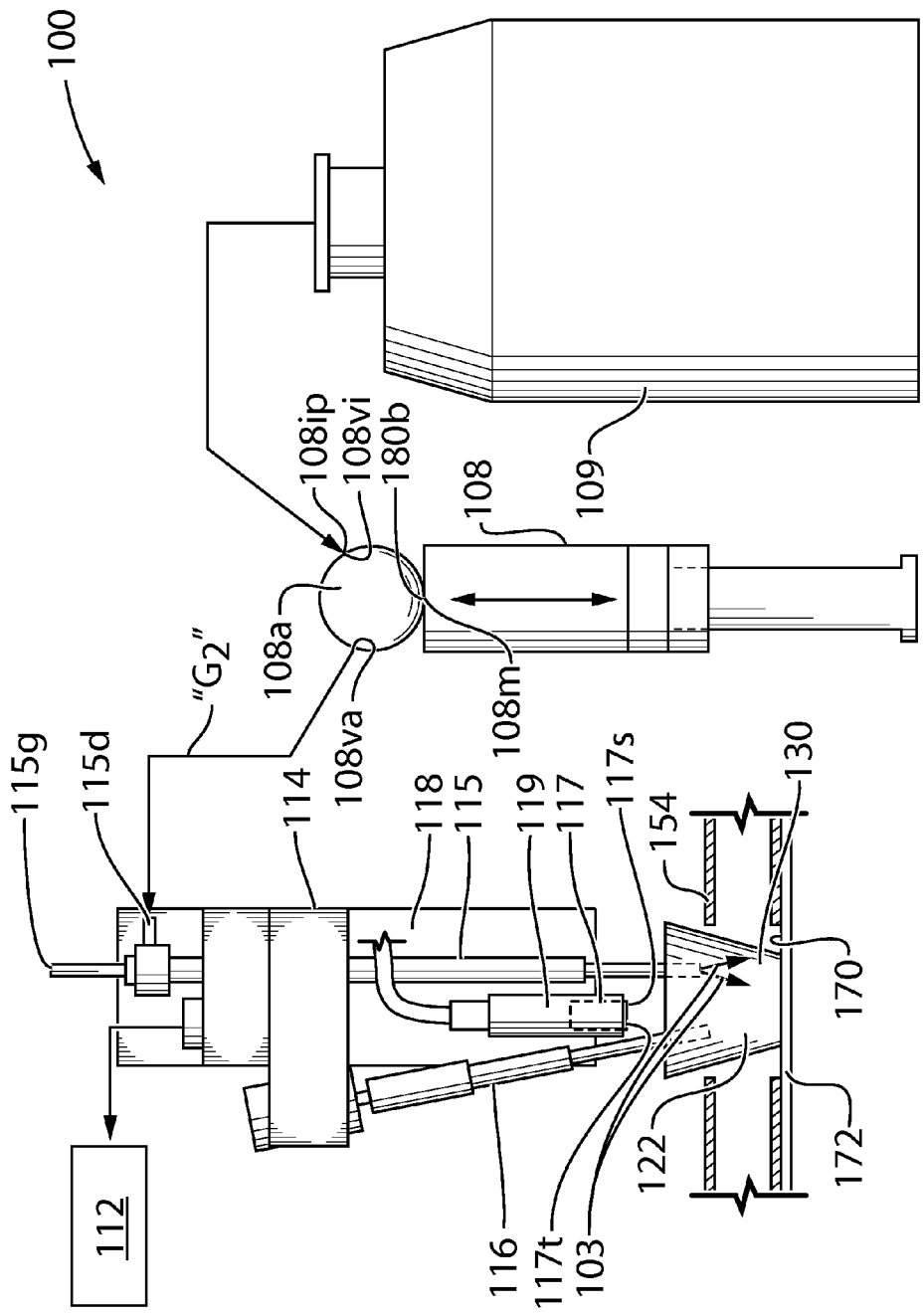
FIG. 13 is a front elevational view similar to FIG. 12, showing the sampling head with various devices mounted thereon and showing a diluent reservoir, a diluent syringe, and a delivery and uptake tube apparatus in use.
Figure 14:
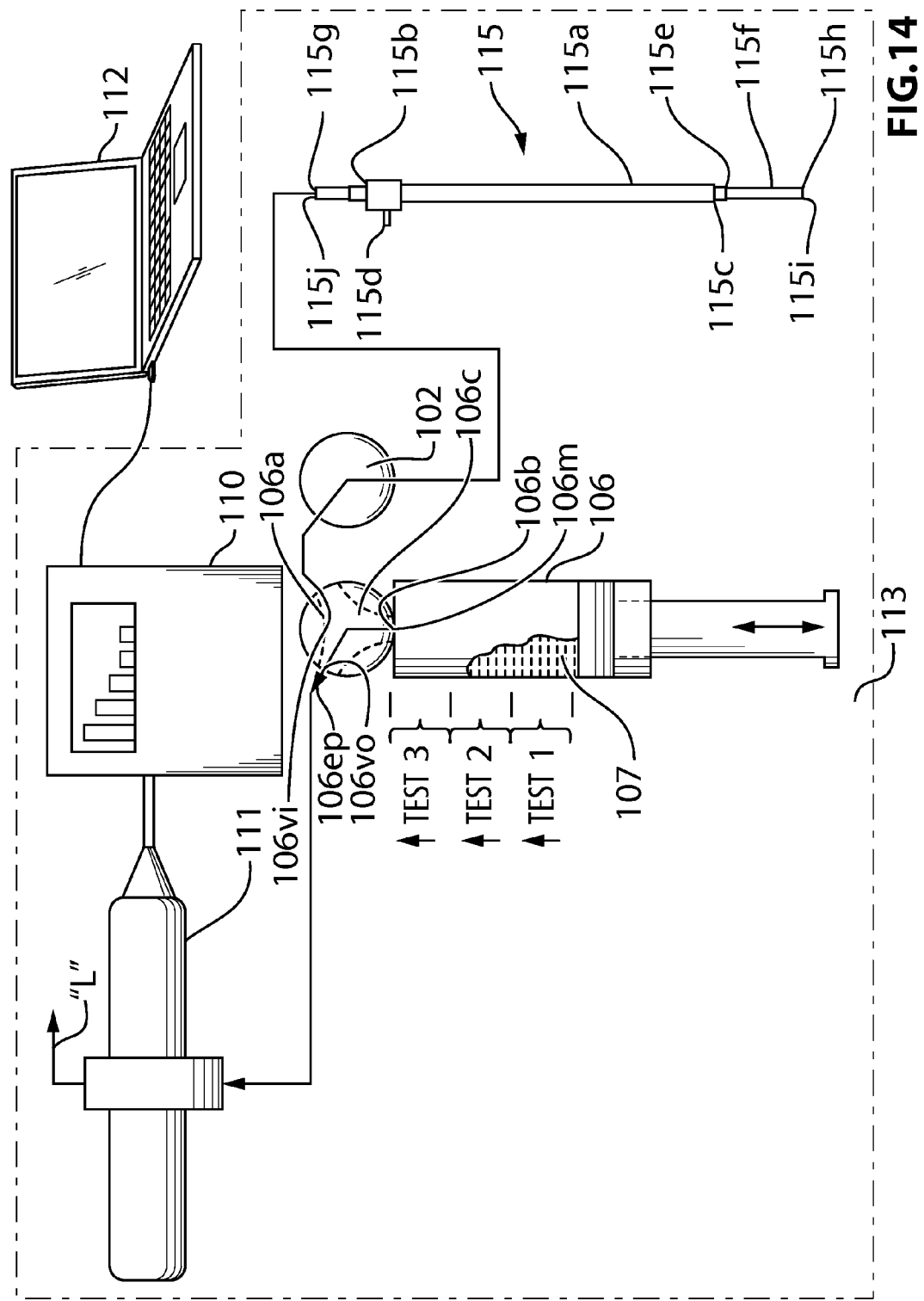
FIG. 14 is a diagrammatic sketch showing other components of The system of FIG. 1.

As can be best seen in FIGS. 13 and 14, the system 120 interacts with a prior art automated optical particle counter 110, and includes a computer/CPU 112 connected in data transfer relation to the automated optical particle counter 110 (which includes an optical sensing cell 111), a sampling head 114, a delivery and uptake tube apparatus 115, the slow speed mixer 116, a small and accurate ultrasonic measuring device 117 having an ultrasonic transducer 117*t* and an ultrasonic sensor 117*s*, a mounting mechanism 118, a mixture syringe 106, a diluent syringe 108, and a diluent reservoir 109, which will typically, as shown in the figures, be remotely located from the other components shown in FIG. 1. In the exemplary embodiment illustrated, the mixture syringe 106, the diluent syringe 108, the optical particle counter 110, which includes the optical sensing cell 111, are preferably located within, or mounted on, the housing 113. They may, however, also be located remotely from the housing 113, with the use of suitable tubing and cabling used to extend their operative connections, as per design choice.

The sampling head 114 has mounted on it for movement therewith, and a delivery and uptake tube apparatus 115, a slow speed mixer 116 in horizontally movable relation on a horizontally oriented "X-Y" reference frame 127, for controlled two-dimensional movement in a horizontal "X-Y" coordinate grid over the container positioning member 150, the sample containers 130, and the reference surface 170 when The system 120 of the present invention is in its in-use sampling configuration for use with the automated optical particle counter 110 as described herein.

More specifically, the system 120 provides for the automated dilution and delivery of a plurality of mixtures 107 of diluent 103 and liquid samples 122 respectively disposed in an equal plurality of congruent sample containers 130 to sampling cell 111 of the optical particle counter 110. The congruent sample containers 130 each have an upwardly facing open mouth 142 through which liquids may enter the exit the congruent sample containers 130. The system also comprises a container positioning member 150 for receiving and retaining the congruent sample containers 130 in an array. The array is preferably regularly and evenly spaced, and is based on a perpendicular "X-Y" reference system, or in other words, a quadrilateral array. Other patterns or arrangement of arrays are also acceptable and within the scope of the present invention.

A respective unknown volume of liquid sample 122 has been poured into each sample container 130, as can be best seen in FIGS. 16 and 17. Typically, the unknown volume of liquid sample 122 is manually poured by an operator (without the need of a pipette) from a sample bottle 101, as seen in FIG. 16. Typically each sample bottle 101 will contain a unique liquid sample 122 originating from a unique identified source, which source information will be tracked throughout the testing process as per usual laboratory procedures. The unknown volume of each liquid sample 122 may be approximated by visual estimation of the operator with respect to indicia 131 marked on the sidewall of each of the sample containers 130.

The unknown volume of each liquid sample 122 must essentially be less than a pre-determined threshold volume determined to be a useful overall volume to use with the optical particle counter 110. As can be readily understood, the pre-determined threshold volume is necessarily also less than the total volume of the respective sample container 130.

The system 120 also comprises an automated diluent pumping mechanism 108 having a diluent ingress port 108*ip*, and a diluent egress port 115*e*. More specifically, the diluent pumping mechanism 108 preferably comprises a diluent syringe 108 having a mouth 108*m*, and a valve 108*a* connected in leak-proof relation to the diluent syringe 108 at the mouth 108*m*. The valve 108*a* has a valve inlet 108*vi*, a valve outlet 108*vo*, and a syringe opening 108*b*. The valve inlet 108*vi* is in fluid communication with the diluent ingress port 108*ip* and the valve outlet 108*vo* in fluid communication with the diluent egress port 115*e*. The syringe opening 108*b* connects the valve inlet 108*vi*, the valve outlet 108*vo*, and the mouth 108*m* of the diluent syringe 108 in fluid communication with each other.

Figure 18:
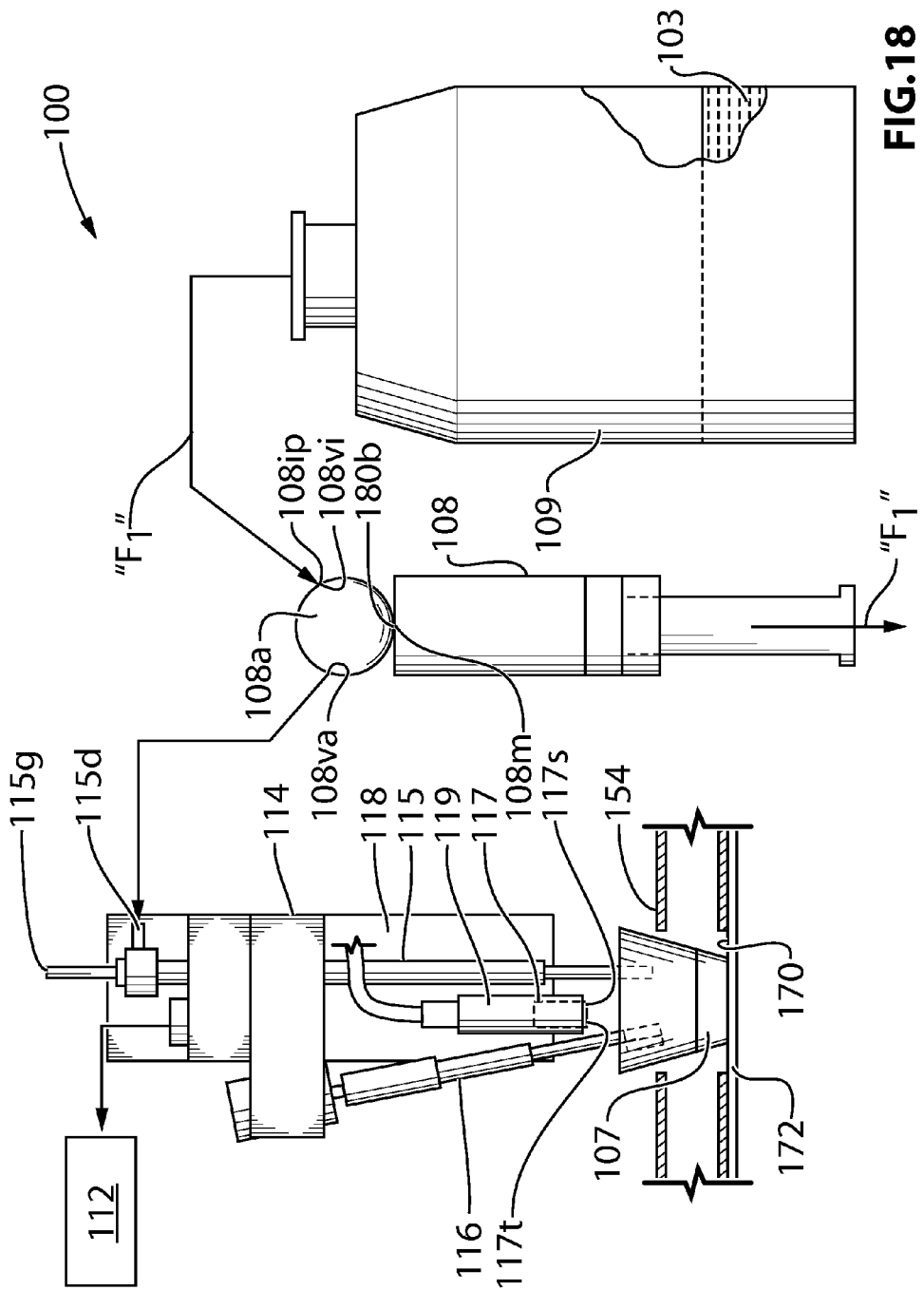
FIG. 18 is a front elevational view similar to FIG. 13, showing a respective volume of a suitable diluent being drawn from a diluent source.
Figure 19:
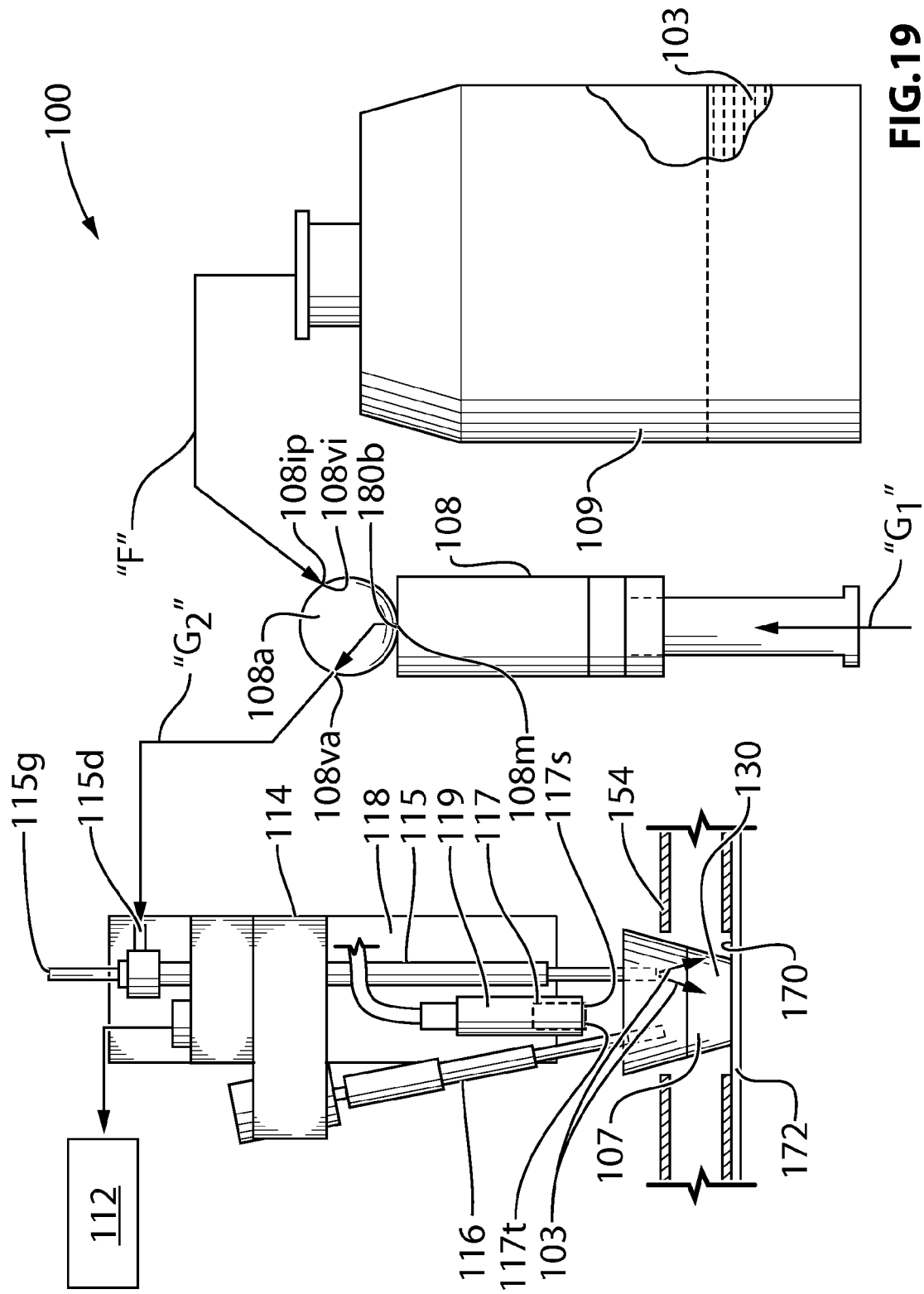
FIG. 19 is a front elevational view similar to FIG. 18, showing a drawn volume of diluent being introduced into a congruent sample container though its open mouth.
Figure 20:
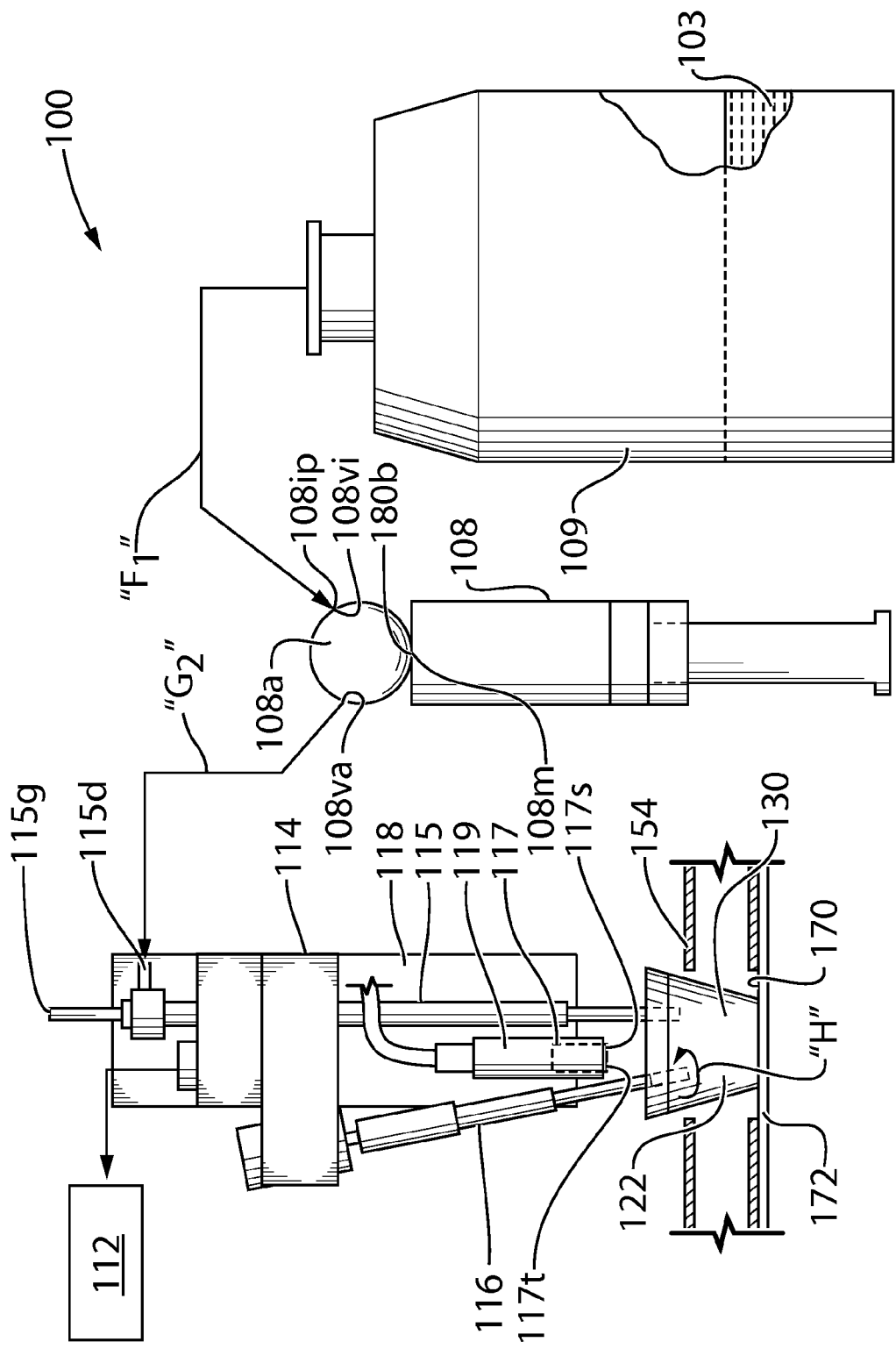
FIG. 20 is a front elevational view similar to FIG. 19, showing the mixture of liquid sample and diluent in the congruent sample container being agitated by a mixer.

The diluent ingress port 108*ip* is in fluid communication with a diluent source 109 shown in FIGS. 13, 18 and 19, as diluent reservoir 109. In the preferred embodiment as illustrated, the diluent egress port comprises an outlet 115*e* of an outer diluent tube 115, that is part of the delivery and uptake tube apparatus 115. The diluent egress port 115*e* is positionable in programmed sequence, as controlled by the computer/CPU 112, over the open mouth 142 of each of the congruent sample containers 130 retained in the array.

The automated diluent pumping mechanism 108 is adapted as described for drawing a respective volume of a suitable diluent from the diluent source 109, and for introducing the drawn volume of the diluent 107 though the open mouth 142 of each sample container 130 for mixing with the respective unknown volume of the liquid sample 122 placed within each sample container 130 to together form a mixture 107 of the diluent 107 and liquid sample 122 for testing by the optical particle counter 110. The volume of the mixture 107 in each sample container 130 should be substantially equal to the pre-determined threshold volume.

The system 120 further comprises an automated mixture pumping mechanism that preferably comprises an electrical motor driven mixture syringe 106 having a mixture ingress port 115i (on uptake tube apparatus—see FIG. 15), and a mixture egress port 106ep. More specifically, the mixture pumping mechanism preferably comprises the mixture syringe 106 having a mouth 106m, and a valve 106a connected in leak-proof relation to the mixture syringe 106 at the mouth 106m. The valve 106a has a valve inlet 106vi, a valve outlet 106vo, a syringe opening 106b and a central chamber 106c. The valve inlet 106vi is in fluid communication with the mixture ingress port 115i, and the valve outlet 106vo is in fluid communication with the mixture egress port 106ep. The central chamber 106c connects the valve inlet 106vi, the valve outlet 106vo, and the syringe opening 106b in fluid communication with each other. The syringe opening 106b and the mouth 106m of the mixture syringe 106 connect the valve 106a and the syringe 106 in fluid communication one with the other.

Figure 15:
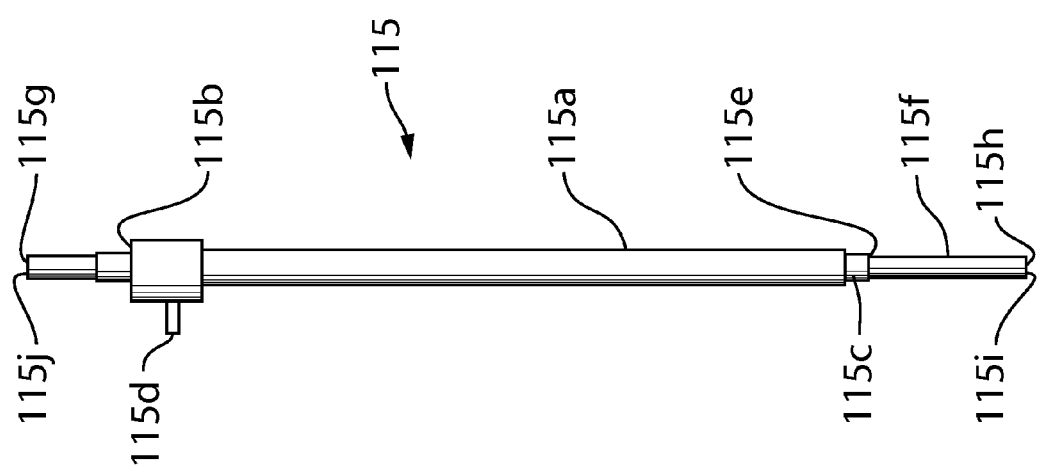
FIG. 15 is an enlarged side elevational view of one of the components of FIG. 14, being a delivery and uptake tube apparatus.
Figure 21:
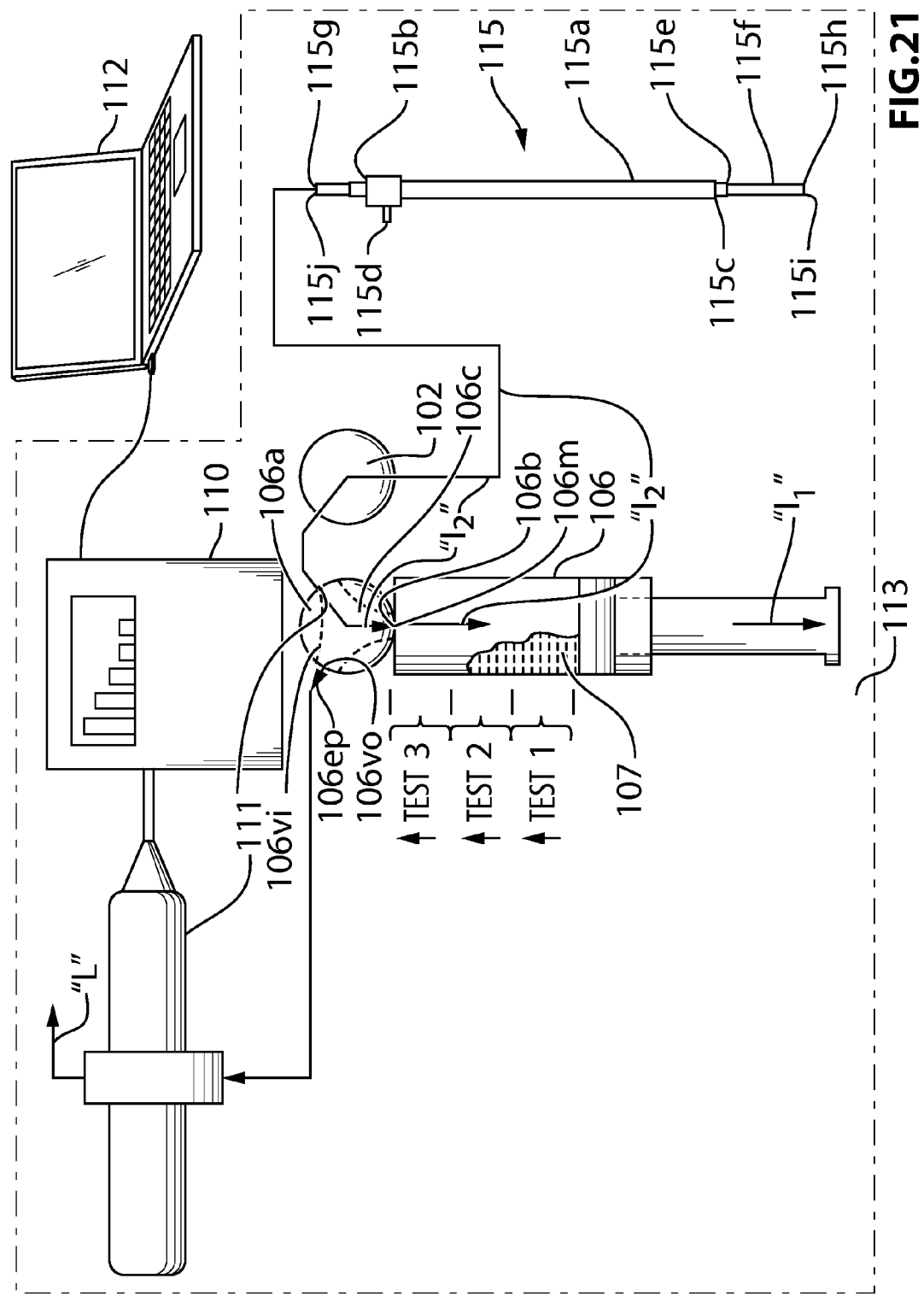
FIG. 21 is a diagrammatic sketch similar to FIG. 14, showing a respective volume of mixture of liquid sample and diluent being sequentially drawn from a congruent sample container; and, FIG. 22 is a diagrammatic sketch similar to FIG. 21, showing a respective drawn volume of mixture of the diluent and liquid sample the being delivered to an optical particle counter.
Figure 22:
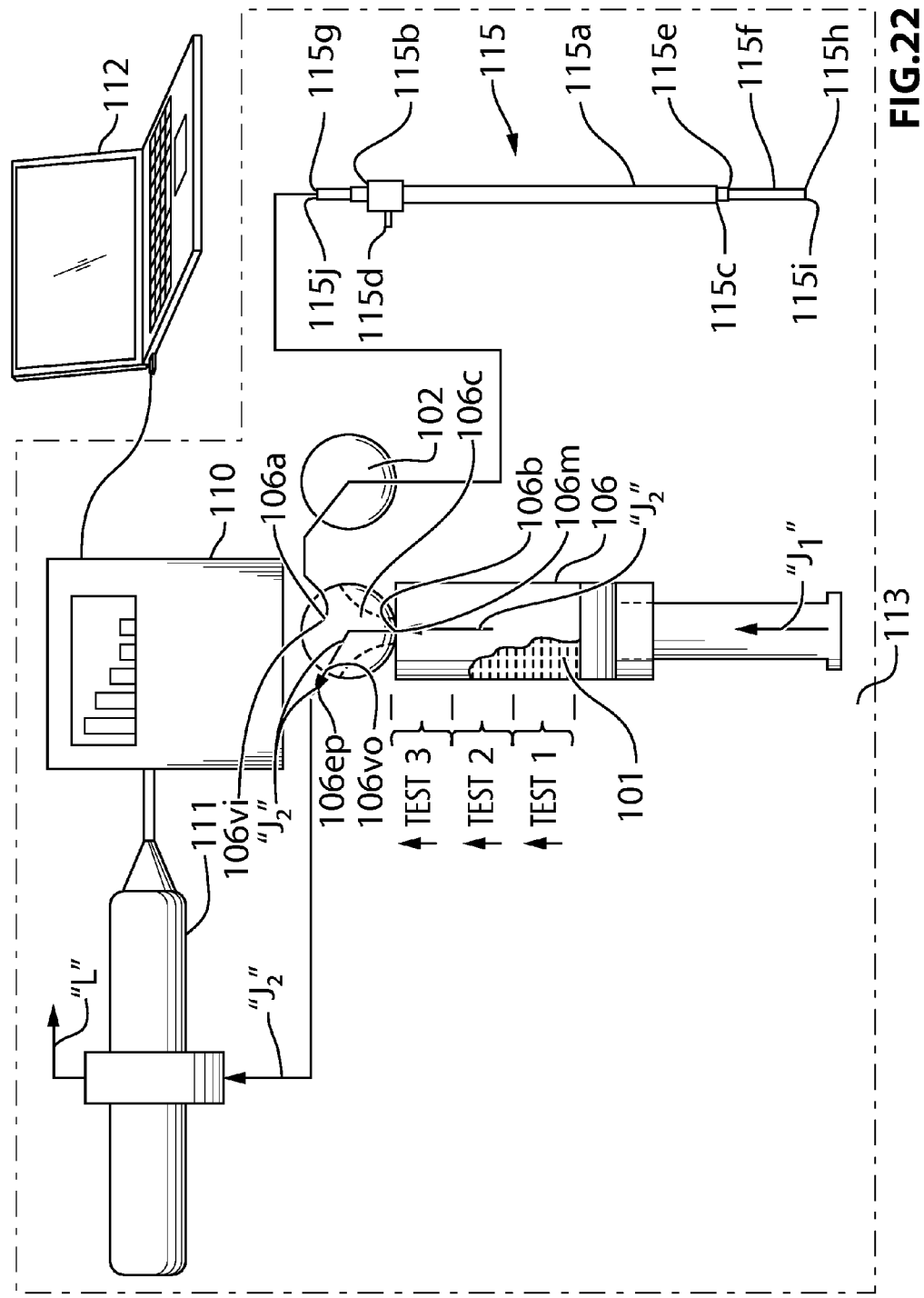

The mixture egress port 106ep is also in fluid communication with the optical sensing cell 111 of the optical particle counter 110, as can be best seen in FIGS. 14, 21 and 22. In the preferred embodiment illustrated, the mixture ingress port 115i comprises an inlet 115i disposed at the bottom end 115h of the uptake tube apparatus, as best seen in FIG. 15. The mixture ingress port 115i is positionable in programmed sequence over the open mouth 142 of each of the congruent sample containers 130 retained in the array so as to be in fluid communication with the mixture 107 of diluent 103 and liquid sample 122 in each congruent sample container 130.

As described, the automated mixture pumping mechanism is for sequentially drawing a respective volume of mixture 107 of diluent 103 and liquid sample 122 from the sample containers 130 and for delivering the respective drawn volume of mixture 107 of diluent 103 and liquid sample 122 to the optical particle counter 110.

The system 120 further comprises the computer/CPU 112, that is connected in data communicating relation to the ultrasonic measuring device 117. Any suitable type of computer/CPU 112 could be used, from a portable dedicated handheld unit, through a laptop computer, or a desktop computer, through a mainframe computer. The terms "computer", "central processing unit" and "computer/CPU" are used interchangeably in this specification and the claims appended hereto, as will be understood by those skilled in the art. The computer/CPU 112 is programmed, inter alia, to electronically measure the vertical position of the top surface 122t of the liquid sample 122 in each selected sample container 130 with respect to the measurement device, namely the ultrasonic measuring device 117. The computer/CPU 112 is also programmed to electronically calculate an accurate height measurement of the top surface 122t of the liquid sample 122 in the selected sample container 130 with respect to an upwardly directed planar reference surface 170, using the measurement of the vertical position of the top surface 122t of the liquid sample 122. The accurate height measurement of the top surface 122t of the liquid sample 122 in the selected sample container 130 with respect to an upwardly directed planar reference surface 170 is calculated by means of determining the vertical difference between the vertical position of the top surface 122t of the liquid sample 122 and the vertical position of the upwardly directed planar reference surface 170.

The computer/CPU 112 is also programmed to electronically calculate the unknown volume of the liquid sample 122 in the selected sample container 130 using the aforesaid accurate height measurement combined with the known geometry of the congruent sample containers 130. The congruent sample containers 130 as illustrated are frustum shaped, which makes the calculation of the internal volume of the containers at any particular height relatively straight forward, as would be well known by one skilled in the art.

The computer/CPU 112 is further programmed to electronically calculate the volume of diluent to add into the selected sample container 130 necessary to obtain the pre-determined threshold volume of the mixture 107, based on the difference between the volume of the liquid sample 122 in the selected sample container 130 and the pre-determined threshold volume. The computer/CPU 112 is further programmed to electronically calculate the volume of diluent to add into the selected sample container 130 to obtain the pre-determined threshold volume of the mixture 107, as aforesaid, based on the viscosity of the liquid sample 122. Alternatively, the computer/CPU 112 is programmed to electronically calculate the volume of the liquid sample 122 in the selected sample container 130 based on a calibration graph of sample height versus sample volume. Further, the computer/CPU 112 is further programmed such that the pre-determined threshold volume of the mixture 107 is substantially the same volume for each sample container 130.

If desired, a further step can be included. More specifically, the computer/CPU 112 can be further programmed to electronically calculate the dilution ratio of the unknown volume of diluent 103 and liquid sample 122 in the sample container 130. If the dilution ratio of the unknown volume of liquid to the diluent is between about 1:0 and 1:9, the subsequent step of agitating the mixture 107 of the diluent 103 and liquid sample 122 can also be performed.

The computer/CPU 112 is further programmed to electronically control the speed of the slow speed mixer 116. The slow speed mixer 116 is for agitating the mixture 107 of the diluent 103 and liquid sample 122 in the sample containers 130. Controlling the speed of the mixer 116 is important in order to accommodate various pre-determined threshold volumes, various sizes of congruent sample containers 130, and also various viscosities of liquid samples 122.

In order for the above described functions to be performed, the sampling head 114, the delivery and uptake tube apparatus 115, the slow speed mixer 116, and the small and accurate ultrasonic measuring device 117 must be horizontally and vertically movable over the horizontally oriented "X-Y" reference frame 127. The sampling head 114, the delivery and uptake tube apparatus 115, the slow speed mixer 116, and the small and accurate ultrasonic measuring device 117 are preferably operatively mounted in horizontally and vertically movable relation on the reference frame 127 by the mounting mechanism 118. The diluent ingress port 108ip, the diluent egress port 115e and the mixer are mounted on the sampling head 114, that is itself mounted in vertically movable relation on the horizontally oriented "X-Y" reference frame 127 by means of a mounting mechanism 118.

Fundamentally, the horizontally oriented "X-Y" reference frame 127 is for operatively mounting the diluent egress port 115e, the mixture ingress port 115i and the mixer 116 in horizontally movable relation for controlled two-dimensional movement in a horizontal "X-Y" coordinate grid over the container positioning member 150. Further, the "X-Y" reference frame 127 carries the mounting mechanism 118, to which the sampling head 114 is operatively mounted, for controlled movement in a vertical "Z" direction with respect to the "X-Y" reference frame 127 and the container positioning member 150. The overall horizontal and vertical movement may also be considered as three-dimensional movement in an "X-Y-Z" reference frame.

The horizontally oriented "X-Y" reference frame 127 comprises a first horizontal track 127a and a second horizontal track 127b oriented substantially perpendicularly one to the other. The mounting mechanism 118 is mounted in horizontally movable relation on the horizontally oriented "X-Y" reference frame 127, and more specifically, mounted in horizontally movable relation in a "Y"-direction on the first horizontal track 127a. The first horizontal track 127a is mounted on the second horizontal track 127b in horizontally movable relation in an "X"-direction that is perpendicular to the "Y"-direction.

The system 120 further comprises an "X"-horizontal-movement motor 127x for moving the first horizontal track 127a in horizontally movable relation in the "X"-direction along the second horizontal track 127b, a "Y"-horizontal-movement motor 127y for moving the mounting mechanism 118 in horizontally movable relation in the "Y"-direction along the first horizontal track 127a, and a "Z"-vertical-movement motor 127z for moving the sampling head 114 in vertically movable relation in the "Z"-direction along the mounting mechanism 118. The "X"-horizontal-movement motor 127x, the "Y"-horizontal-movement motor 127y, and the "Z"-horizontal-movement motor are each controlled by suitable software executed by the computer/CPU 112 and are independently movable one with respect to the other.

The delivery and uptake tube apparatus 115, which is best shown in enlarged isolated format in FIG. 15, is mounted on the sampling head 114. As will be seen in the Figures, the diluent ingress port 108ip and the diluent egress port 115e are part of the delivery and uptake tube apparatus 115. In the preferred embodiment illustrated, the delivery and uptake tube apparatus 115 comprises an outer diluent tube 115a and an inner delivery tube 115f. The outer diluent tube 115a has a top end 115b and a bottom end 115c, with an inlet 115d disposed adjacent the top end 115b and an outlet 115e comprising a plurality of jets disposed adjacent the bottom end 115c. The inlet 115d is connected in fluid communication to the diluent syringe 108 through the line indicated by arrow "$G_2$" in FIG. 13. The inner delivery tube 115f has a top end 115g and a bottom end 115h, with an inlet 115i disposed adjacent the bottom end 115h and an outlet 115j disposed adjacent the top end 115g. The outlet 115j is connected in selective fluid communication to the input side of the optical sensing cell 111 of the optical particle counter 110, as described more fully below.

This double tube arrangement keeps separate the sample mixture 107 and diluent 103 supply streams. Accordingly, diluent enters the outer diluent tube 115a near the top end 115b through the inlet 115d and flows from the outer diluent tube 115a over the inner delivery tube 115f, and egresses from the outer diluent tube 115a through the outlet 115e positioned at the bottom end 115c. Liquid sample 122 enters the inner delivery tube 115f through the inlet 115i disposed at the bottom end 115h and egresses the inner delivery tube 115f through the outlet 115j disposed adjacent the top end 115g. The inner delivery tube 115f is slidably mounted within the outer diluent tube 115a in fixed final relation thereto.

In conjunction with the system 120 of the present invention, an automated optical particle counter 110 performs automated particle counts of mixtures 107 of diluent 103 and liquid samples 122 presented by the system 120 and contained within the plurality of substantially congruent sample containers 130. As an integral part of the process, the volume of liquid sample 122 in each sample container 130 must be determined with considerable accuracy in order to achieve an accurate particle count. Further, the amount of diluent 103 to add to the unknown volume of liquid sample 122 must be calculated accurately, and must be added accurately to the liquid sample 122. It has been found that the system 120 of the present invention produces a potential sample volume error of less than 2%, which is well within acceptable tolerances for the ASTM-D7647 test method, and which tolerance level has not been achieved in the prior art, so far as automated liquid sample 122 dilution and presentation systems are concerned.

In order to accurately perform volumetric calculations of liquid sample 122 in the sample containers 130 received and retained by the cup positioning member 150, the ultrasonic measuring device 117 with its ultrasonic transducer 117t and its ultrasonic sensor 117s is used. The ultrasonic measuring device 117 uses very small sensor (VSS) technology, and is used to accurately measure the height of liquid in each of the congruent sample containers 130 tested. The ultrasonic measuring device 117 is preferably incorporated into a plastic mounting member 119 mounted adjacent the bottom end 118a of the mounting mechanism 118 that carries the moveable sampling head 114. Data can be obtained from the ultrasonic sensor and is used by the computer/CPU 112 to quickly and accurately calculate the volume of liquid sample 122, such as used oil, to be tested in each congruent sample container 130 immediately before proceeding with dilution of each liquid sample 122.

Generally speaking, for each congruent sample container 130 containing a liquid sample 122, the measurement mechanism, namely the transducer 117t and the sensor 117s of the ultrasonic measuring device 117, is moved into place in a fixed "X-Y" coordinate position directly over the unknown volume of liquid sample 122 in the sample container 130. An ultrasonic wave is emitted from the ultrasonic transducer 117t, and is reflected from the surface of the liquid 122 in the sample container 130. The reflected ultrasonic wave is received back at the sensor 117s and the time difference between emission and reflection is measured, and is used to determine the height of the top surface 122t of the liquid 122. Once the height of the top surface 122t of the liquid 122 in the congruent sample container 130 is established in this manner, the volume of liquid 122 in the sample container 130 can be determined from the geometry of the sample container 130. Thereafter, the volume of diluent 103 that will be needed to dilute the liquid sample 122 to a final volume for testing, can then be calculated by the computer/CPU 112 and automatically added to the liquid sample 122 in the sample container 130. It has been found that a suitable diluent is one such as a solvent comprising, for example, 75% toluene and 25% Propan-2-ol.

Reference will now be made to FIGS. 5 through 11, which figures show the congruent sample containers 130 being prepared and presented for batch testing according to the present invention. FIG. 5 shows an empty congruent sample container 130 about to have an unknown volume of liquid sample 122 poured into it, and sequentially FIG. 6 shows a sample container 130 having about seventeen (17) milliliters of liquid sample 122 having been manually poured by optical estimation by a laboratory technician into it, after the liquid sample 122 has been sufficiently pre-mixed in the sample bottle 101 to evenly distribute any contaminants. FIGS. 7 through 11 show a plurality of congruent sample containers 130 retained by the container positioning member 150 being manipulated into place on the reference surface 170. While a liquid sample 122 having a volume of about seventeen (17) milliliters has been manually poured into each of the congruent sample containers 130 by a laboratory technician without pipetting, the exact volume is unimportant, so long as the volume is below the pre-determined threshold volume of thirty (30) milliliters.

The main operational advantage of the present invention, namely the system 120, is that it allows approximate volumes of oil samples that are to be tested to be manually poured by laboratory personnel directly into congruent sample containers 130. This method of directly pouring the oil samples into the congruent sample containers 130 is quick, simple, and easy. Most importantly, it also eliminates the use of a pipette for handling of the liquid samples 122 and of the diluent, thereby ameliorating, or even entirely eliminating, the known disadvantages associated with pipetting, as mentioned previously, namely a high labour content and associated costs, lack of availability of labour during off hours, slowness of the process, and repetitive strain injuries to pipetting personnel.

Figure 7:
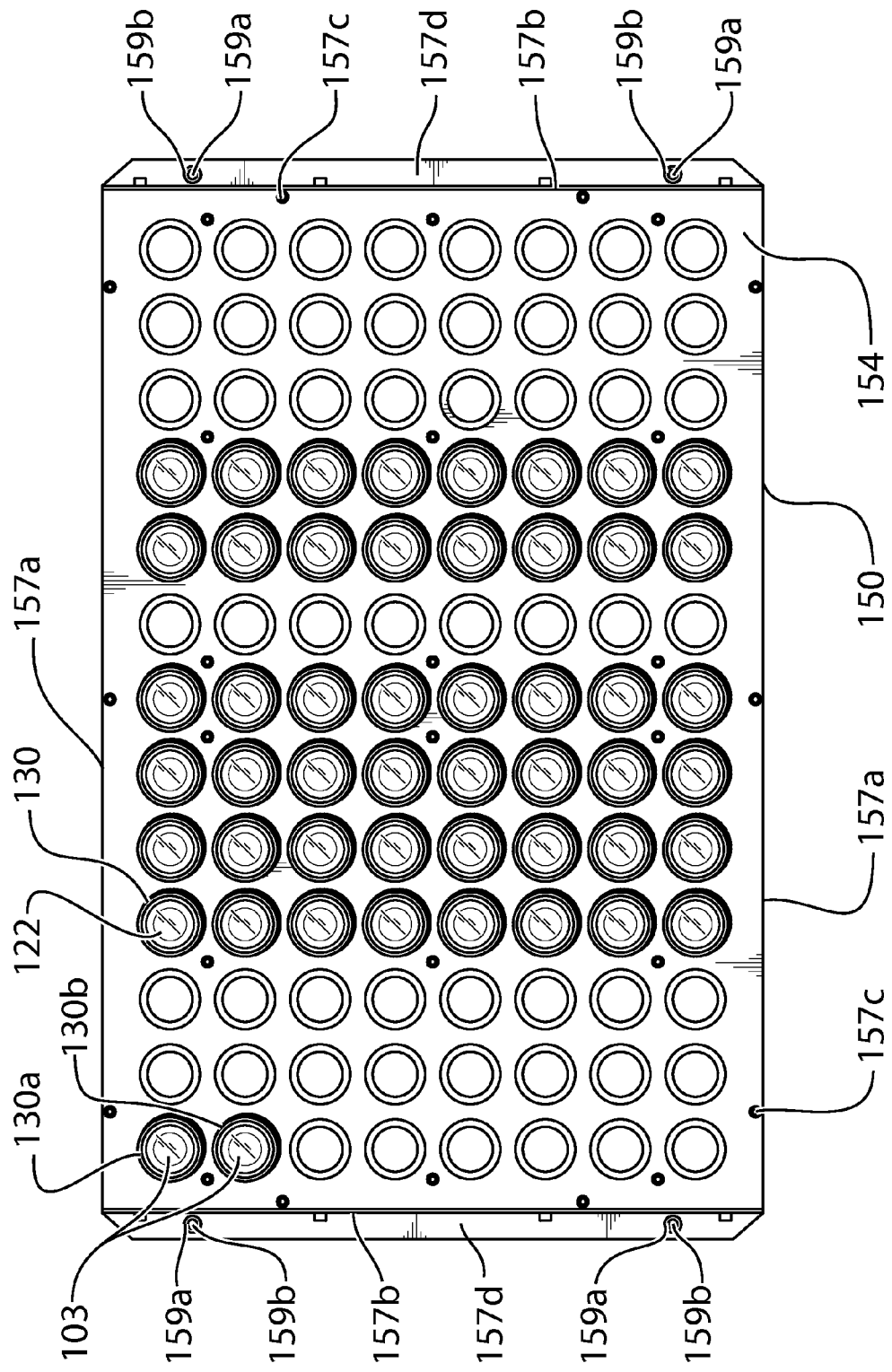
FIG. 7 is a top plan view similar to FIG. 4, but with the congruent sample containers of FIG. 1 in place therein.

FIG. 7 is a top plan view of the container positioning member 150 and a plurality of congruent sample containers 130, and shows that the first two positions 130a and 130b may contain empty congruent sample containers 130, as they may be used for storing diluent and for system cleanliness verifications. Diluent 103 from the reservoir 109 (see FIG. 13) is delivered to the sample container 130a in position number "one" (i.e., Column 1, Row 1 in FIG. 7) and used to flush the delivery tubing and the optical sensing cell 111 of the optical particle counter 110 prior to diluent verification. Further, diluent 103 from the reservoir 109 is dispensed to the sample container 130b in position number "two", (i.e., Column 1, Row 2 in FIG. 7) for example, and twenty-five (25) milliliters of this diluent aspirated to the mixture syringe 106.

In order to determine the volume of liquid sample 122 in the sample container 130 being tested, and also to determine the volume of diluent 103 that will be needed to dilute the liquid sample 122 to a pre-determined threshold volume for testing of, for example, thirty (30) milliliters, data from the ultrasonic height sensor 117 in the sampling head 114 is transferred to the computer/CPU 112. A batch file containing the position of the cup positioning member 150 and other information related to the liquid sample 122 in the congruent sample containers 130 is stored on the computer/CPU 112 controlling the automated optical particle counter 110.

Depending on the viscosity and expected cleanliness of the liquid sample 122, each liquid sample 122 is preferably diluted before testing by means of the addition of a suitable diluent (solvent) added to each sample container 130 such that the volume of diluent 103 added is preferably between three (3) milliliters (1:10 dilution) and fifteen (15) milliliters (1:1 dilution), assuming a thirty (30) milliliter sample container 130 is utilized. The diluent 103 and the liquid sample 122 must then be agitated in order to fully mix the diluent 103 and the liquid sample 122 to create the mixture 107. In order to accomplish this, the sampling head 114 moves under control of the computer/CPU 112 down into the sample container 130 and the slow speed mixer 116 is started. The required volume of diluent 103 is then added to the sample container 130 through the diluent tube 115a to dilute the liquid sample 122, as previously explained (see FIG. 13). The diluent 103 and the liquid sample 122 are mixed under control of the computer/CPU 112 for a specified time period to dissolve the diluent 103 and liquid sample 122 and suspend the various particulates.

After the mixing period expires, the mixture syringe 106 is programmed to draw a volume of approximately six (6) milliliters of mixture 107 from the sample container 130 through the delivery uptake tube apparatus 115 and into the mixture syringe 106. The mixture syringe 106 is then programmed to dispense the volume of six (6) milliliters to the optical sensing cell 111 and to eject displaced air from the syringe 106, and to thereafter flush the optical sensing cell 111 with about three (3) milliliters of a new mixture sample. A further volume of approximately twenty-three (23) milliliters of new mixture sample 107 is then aspirated to the mixture syringe 106. The valve 106a is switched by the computer/CPU 112 to isolate the inlet port 106b of the syringe 106. The mixture syringe 106 is further programmed to aspirate a small additional volume of mixture 107 against the closed inlet port 106b in order to create a partial vacuum in the syringe 106 and thereby degas the mixture 107. After a specified degassing period, the mixture syringe 106 is programmed to dispense the additional volume of mixture 107 to the optical sensing cell 111 to restore near normal pressure.

Once the mixture 107 has been degassed as aforesaid, the sample analysis takes place within the optical sensing cell 111 according to the know processes of such devices. Three separate tests as just described are preferably conducted sequentially by the optical particle counter 110. In each of the three tests, a five (5) milliliter samples of the mixed diluent liquid sample is analyzed. The data set is tested for ASTM D7647 validity and an average particle count and distribution result is calculated by the computer/CPU 112. All measured and calculated data is stored in a sample specific text file in the computer/CPU 112 for subsequent processing time by the operator. Subsequent to each test, the mixture 107 is expelled from the optical sensing cell 111 of the particle counter 110, as indicated by arrow "L" in FIGS. 14, 21 and 22.

In the embodiment illustrated, the system, as indicated by the general reference numeral 120, is used for the automated dilution and delivery of a plurality of mixtures 107 of diluent 103 and liquid samples 122 respectively disposed in an equal plurality of congruent sample containers 130 to an optical particle counter 110. The congruent sample containers 130 are substantially identical to one another and are, preferably, cup-like in shape (without a handle) and may, for reasons of availability and economy, be the same as, or similar to, the well known plastic pill containers used in hospitals and the like to dispense a dosage of pills or other medicine to patients of such facilities. In any event, each container 130 has a base 132, and a continuous sidewall 134 that is preferably annular in shape so that the rotational orientation of each congruent sample container 130 during use is not relevant. Preferably, but not essentially, the congruent sample containers 130 are each frustum shaped. As can be best seen in FIGS. 5, 6, 8 and 9, the continuous sidewall 134 of the congruent sample containers 130 each has an inner wall surface 136 and an outer wall surface 138, and extends upwardly from the base 132 to terminating at a top end 140 to thereby define the upwardly facing open mouth 142. There is also an engagement portion 144 of the outer wall surface 138 that is wider than the base 132 and closer to the mouth 142 than to the base 132. The engagement portion 144 is dimensioned for engaging the container positioning member 150, in one configuration (only) of the container positioning member 150, as will be discussed subsequently in greater detail.

Further, the container positioning member 150 comprises a horizontally extending main body portion 152. In the preferred embodiment, as illustrated, the main body portion 152 preferably, but not essentially, comprises an upper plate 154 and an optional lower plate 156, which may be connected together in secure relation by peripheral side walls 157a and peripheral end walls 157b and by a plurality of spacers 158.

The upper plate 154 and the lower plate 156 may be secured together via the peripheral side walls 157a and peripheral end walls 157b by threaded fasteners 157c. Further, the upper plate 154 and the lower plate may be secured together via the plurality of spacers 158 by threaded fasteners 158c. There are also preferably provided two horizontally outwardly projecting end flanges 157d disposed one flange at each end of the main body portion 152.

The upper plate 154 and the lower plate 156 are each preferably substantially planar and substantially parallel one to the other. For the sake of strength and rigidity, the main body portion 152 is made substantially from metal components and, preferably from aluminium-based materials, or from stainless steel-based materials. Alternatively, the container positioning member 150, and/or any of the components thereof, may be made from any other suitably rigid and robust material.

As can best be seen in FIGS. 8 and 9, the main body portion 152 of the container positioning member 150 comprises a plurality of substantially vertically disposed container-receiving sockets 160 formed in the main body portion 152. Preferably, the substantially vertically disposed container-receiving sockets 160 are arranged in an ordered array, or in other words, a rectangular matrix pattern, in order to simplify the positioning of the sampling head 114 during use of The system 120. Further, the substantially vertically disposed container-receiving sockets 160 are substantially annular in plan outline, in order to help control and minimize the vertical and lateral movement of the congruent sample containers 130 during use.

Each of the container-receiving sockets 160 preferably has a top end 162 and a bottom end 164, and is open at the top end 162 and the bottom end 164, in order to permit a sample container 130 to extend therethrough. Each container-receiving socket 160 is defined at the top end 162 by a container-receiving rim portion 166. In the preferred embodiment illustrated, each of the substantially vertically disposed container-receiving sockets 160 comprises an upper container-receiving aperture 168 in the upper plate 154 and a lower container-receiving aperture 169 in the lower plate 156 in axial alignment with the upper container-receiving aperture 168 (best seen in FIGS. 10 and 11).

The container positioning member 150 further comprises a plurality of feet 159 projecting downwardly from the main body portion 152 at each of the two horizontally outwardly projecting end flanges 157c. As can be best seen in FIGS. 8 and 9, each of the feet 159 is secured in place on the bottom of the two horizontally outwardly projecting end flanges 157c by a co-operating threaded fastener 159a extending downwardly through co-operating through passages (not specifically shown) in the cylinders 159b disposed above the outwardly projecting end flanges 157c and through apertures (not specifically shown) in the horizontally outwardly projecting end flanges 157c, to each threadingly engage one of the feet 159, to thereby secure the feet 159 in a fixed vertical orientation as illustrated.

A corresponding plurality of co-operating foot-locating recesses 124 (see FIGS. 1 and 2) may optionally be formed in opposed side rails 126a of the base member 126 adjacent to the reference surface 170, for receiving the feet 159 in stable indexed relation therein when the container positioning member 150 is placed over the reference surface 170 in the operative in-use configuration (see FIGS. 4, 7, 9, and 11).

The base member 126, which structure may be generally table-like, having parallel front and back rails 126b, 126b rigidly connected to opposed side rails 126a, 126a, with the space between all four rails being occupied by a horizontal base plate 195 rigidly connected to the rails. All four rails 126a, 126a, 126b, 126b preferably stand proud of the horizontal base plate 195, so as to define a cavity of quadrilateral plan outline, in which cavity the reference surface 170 may be located as shown. Ideally, but not necessarily, the reference surface 170 is mounted so as to extend upwardly from within the cavity to approximately the same height as the upper surfaces of the four rails 126a, 126a, 126b, 126b. A set of four legs 126c complete the table-like structure that is the base member 126. The components of the base member 126 are preferably constructed from the same general type of metal materials as is the container positioning member 150.

The base member 126 has a reference surface 170 mounted thereon for adjustment of its horizontal level. Preferably, the reference surface 170 is planar, and may, as shown, be constructed from a sheet of plate glass 172 which presents its upper surface as the reference surface 170. It has been determined by the inventor that a high quality precision formed sheet of plate glass provides a reference surface 170 having a height variation of less than 0.025 mm across its upper surface, which is sufficiently flat for most testing discussed herein at a reasonable cost, as compared to having a similarly dimensioned reference surface constructed from plate metal, the latter of which would typically require a costly machining operation to achieve a similar degree of levelness (i.e. flatness) across its upper surface.

The reference surface 170 may be mounted on the base member 126 for adjustment of its horizontal level as aforesaid by means of at least three gimbal mounts 190 (one of which is illustrated in detail in FIGS. 3A and 3B), atop of which gimbal mounts 190 the reference surface 170, specifically the sheet of plate glass 172, sits. In the embodiment illustrated, four gimbal mounts 190 are positioned adjacent each of the four corners of the reference surface 170 (see FIG. 2). If required, a fifth gimbal mount (not shown) may also be centrally positioned between the four gimbal mounts shown to support the underside of the reference surface 170 adjacent its middle area. This may be particularly advantageous where very large sheets of plate glass are employed.

Each of the four gimbal mounts 190 may comprise a vertically oriented threaded member 193 threadibly engaged in a co-operating threaded aperture 194 in the horizontal base plate 195 of the table frame 126. A concave recess 193r in the top end 193t of the vertically oriented threaded member 193 receives a ball bearing 196 in weight bearing relation. The ball bearing 196 receives a disk member 197 at a downwardly facing recess 198 in weight bearing relation. The disk member 197 resides at least partially within a circular recess 195r in the top surface 195t of the horizontal base plate 195. In this manner, the sheet of plate glass 172 that presents the reference surface 170 rests in vertically adjustable supported relation on the four disk members 197. While a relatively small degree of self-levelling is built into the gimbal mounts 190 as illustrated and described, the vertically oriented threaded members 193 are each independently rotatable to thereby selectively move the four disk members 197 up and/or down, as necessary, to more fully adjust the horizontal level of the reference surface 170 until an operatively acceptable degree of horizontal level of the reference surface 170 is achieved.

In an in-use sampling configuration, as can be best seen in FIGS. 10 and 11, the container positioning member 150 is positioned over the base member 126 and the reference surface 170, with the congruent sample containers 130 each positioned within a respective container-receiving socket 160. More specifically, the congruent sample containers 130 each project through both the upper container-receiving aperture 168 in the upper plate 154 and the lower container-receiving aperture 169 in the lower plate 156. As such, the bases 132 of each of the congruent sample containers 130 project through the bottom ends 164 of the container-receiving sockets 160 at the lower container-receiving aperture 169, to thereby be supported in weight bearing relation by the reference surface 170.

It will also be noted that when the container positioning member 150 is in the in-use sampling configuration, the plurality of substantially vertically disposed container-receiving sockets 160 are positioned, shaped and dimensioned such that a gap 161 exists, as is best seen in FIG. 10, between the engagement portion 144 of the outer wall surface 138 of the congruent sample containers 130 and the container-receiving rim portion 166 of the respective container-receiving socket 160. In this manner, the congruent sample containers 130 have basically been temporarily released from contact with the container positioning member 150 in order to be fully supported by the reference surface 170.

Further, in the in-use sampling configuration, the container positioning member 150 is supported in weight bearing relation adjacent the reference surface 170, by means of its feet 159 engaged in the co-operating foot-locating recesses 124 in the table frame 126 adjacent the reference surface 170.

As can be best seen in FIGS. 8 and 10, when the system is removed from its in-use sampling configuration by, for example, upward removal of the container positioning member 150 from positioning over the reference surface 170, each of the congruent sample containers 130 moves downwardly from its position in the in-use sampling configuration, relative to the container positioning member 150, to be supported by the engagement portion 144 of the outer wall surface 138 contacting the container-receiving rim portion 166 of the respective container-receiving socket 160 in weight bearing relation therewith. The container positioning member 150 and the congruent sample containers 130 retained by the container positioning member 150 with the liquid samples 122 therein can then readily be carried away from the base member 126 by a user.

Reference will now be made to the figures, which show the system 120 according to the present invention in use. As can be best seen in FIGS. 5 and 6, the congruent sample containers 130 are being prepared for testing as a sample batch. FIG. 5 shows an empty sample container 130 ready to have a volume of liquid sample 122 manually poured into it, and sequentially FIG. 6 shows a sample container 130 having about seventeen (17) millilitres of liquid sample 122 having been poured into it from a sample bottle 101, after the liquid sample 122 has been sufficiently mixed in, for example, the sample bottle 101 by the operator to evenly distribute any contaminants. FIGS. 1 and 7 through 11 show a plurality of congruent sample containers 130 retained by the container positioning member 150 in place on the reference surface 170. A liquid sample 122 having a volume of about seventeen (17) millilitres has been poured into each of the congruent sample containers 130. The exact volume is unimportant as long as the volume is below the target volume of thirty (30) millilitres.

As can be seen in FIGS. 8 and 10, when the container positioning member 150 is removed from the in-use sampling configuration, the partially full congruent sample containers 130 are supported by the engagement portion 144 of the outer wall surface 138 contacting the container-receiving rim portion 166 of the respective container-receiving socket 160 in weight bearing relation therewith. This configuration would be realized when, for example, an operator carries the container positioning member 150 and the congruent sample containers 130 to the base member 126 and the associated optical particle counter 110, or removes it therefrom after the optical particle counting testing has been completed. Arrow "A" in FIG. 1 and arrow "B" in FIG. 8 indicate movement of the container positioning member 150 and sample containers 130 contained thereby into the operative in-use configuration by being lowered into position atop the base member 126, as the feet 159 are indexingly received by the co-operating foot-locating recesses 124 formed in each of opposed side rails 126a of the base member 126. As can be best seen in FIGS. 8 and 9, and as shown by arrows "C" in FIG. 9, the congruent sample containers 130 are received by the previously leveled reference surface 170 as the container positioning member 150 moves downwardly into contact with the base member 126, into an in-use sampling configuration. In the in-use sampling configuration, the container positioning member 150 is positioned over the reference surface 170 with the congruent sample containers 130 each positioned within a respective container-receiving socket 160 with the bases 132 of the congruent sample containers 130 projecting through the bottom ends 164 of the container-receiving sockets 160, to be supported in weight-bearing relation by the reference surface 170.

Figure 12:
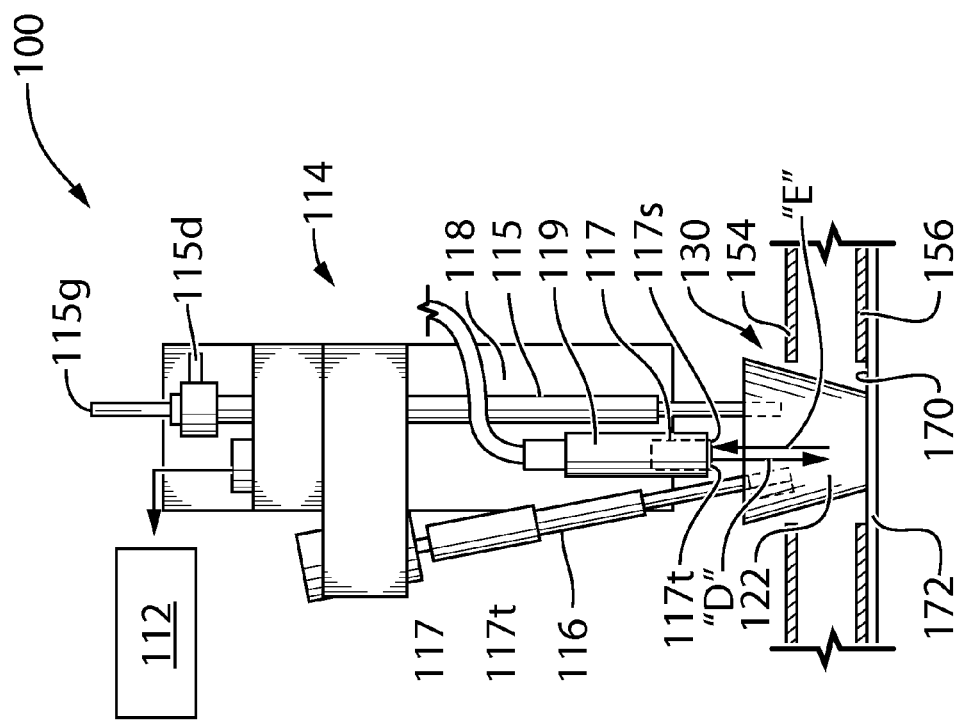
FIG. 12 is an enlarged scale front elevational view of a portion of The system illustrated in FIG. 1, the illustrated portion including a sampling head with various devices mounted thereon.

In the in-use sampling configuration, (see FIGS. 9 and 11) the congruent sample containers 130 are all supported with respect to a substantially level planar surface, namely the reference surface 170. Accordingly, testing errors induced by having the sampling cups supported by an uneven or non-level supporting surface, such as a prior art sample tray, is virtually eliminated. As can be best seen in FIG. 12, the ultrasonic measuring device 117 can take an accurate and meaningful measurement of the height of the top surface 122t of the liquid sample 122 with reference to a substantially level base reference point in each of the congruent sample containers 130, and thereby use this data to accurately calculate the volume of the liquid sample 122 in each of the congruent sample containers 130, and subsequently to calculate the amount of diluent to be added to accurately achieve the desired final volume of the mixture of the liquid sample 122 and the diluent. More specifically, the sampling head 114 is positioned, by means of the "X-Y" reference frame 127 operating under control of the computer/CPU 112, over a selected sample container 130, whereat the ultrasonic measuring device 117 is able to perform a height measurement of the top surface 122t of the liquid sample 122 in the selected sample container 130. In order to accomplish this measurement, the ultrasonic transducer 117t of the ultrasonic measuring device 117 transmits an ultrasonic signal to the top surface 122t of the liquid sample 122 in the selected sample container 130, as indicated by arrow "D" of FIG. 12. The ultrasonic signal is reflected off the top surface 122t of the liquid sample 122, and the reflected signal, as indicated by arrow "E" of FIG. 12, is received by the ultrasonic sensor 117s. Data related to the height of the top surface 122t of the liquid sample 122, as compared to the height of the base 132 of the sample containers 130 supported by the previously leveled reference surface 170, is received by the computer/CPU 112. Based upon the standard geometry of the congruent sample containers 130, the computer/CPU 112 is able to accurately calculate the volume of diluent 103 that needs to be added to the selected sample container 130 in order to produce an overall volume of mixture 107 of thirty (30) millilitres.

Next, with reference to FIG. 18, the necessary quantity of diluent 103 is drawn by the diluent syringe 108 moving in the direction indicated by arrow "$F_1$", from the diluent reservoir 109 through the diluent ingress port 108ip, with the diluent syringe valve 108a open to the diluent reservoir 109 through the valve inlet 108vi, and open to the syringe 108 through the mouth 108m, as indicated by arrows "$F_1$" to "$F_2$". As can be seen in FIG. 19, the diluent syringe valve 108a is then adjusted to be open to the inlet 115d of the outer diluent tube 115a, which is the diluent egress port 115e (see FIG. 15), through the mouth 108m and the valve outlet 108vo. The diluent syringe 108 is then moved (as indicated by arrow "$G_1$", in FIG. 19), to inject the necessary quantity of diluent 103 into the selected sample container 130, as indicated by arrows "$G_2$". The mixer 116 is then used to agitate the liquid sample 122 and the diluent 103 until a substantially uniform mixture 107 is achieved with the various particulates in suspension, as indicated by arrow "H" in FIG. 20.

Subsequently, as can be seen in FIG. 21, an amount of more than twenty-one (21) millilitres of the mixture 107 is drawn, by movement of the mixture syringe 106 (in the direction indicated by arrow "$I_1$") into the mixture syringe 106 from the sample container 130 through the mixture ingress port 115i (as indicated by arrow "$I_2$"), with the mixture syringe valve 106a open to the sample container 130 through the valve inlet 108vi and with the stop valve 102 open to the mixture syringe 106 through the mouth 106m. The mixture 107 is then degassed in a suitable manner, the explanation of which is beyond the necessary scope of the present disclosure, except to say that the stop valve 102 is closed to the ambient surroundings while the mixture syringe 106 is moved again in the direction of "$I_1$". Finally, the mixture syringe 106 is then moved in the direction of arrow "$J_1$" (as seen in FIG. 22) to inject the de-gassed mixture 107 into the optical sensing cell 111 of the automated optical particle counter 110, preferably in three separate test volumes of seven (7) millilitres each, as indicated by arrows "$J_2$".

With this system, the congruent sample containers 130 can be accurately tested in a batch sequence by the automated optical particle counter 110, due to an absence of interference by "soft particles" with the optical sensing cell 111 of the automated optical particle counter 110. It has been found that the present invention produces a potential volume error of less than 2%, which is well within the acceptable tolerances allowed under the ASTM-D7647 test method, and which low level of error is unattainable with prior art automated particle counting systems not involving manual pipetting of the liquid samples 122 and diluents used in testing.

This concludes the description of but one exemplary embodiment of the invention. Many modifications and variations are possible in light of the above teaching and will be apparent to those skilled in the art. The scope of the claims should not be limited by the preferred embodiments set forth in the examples, but should be given the broadest interpretation consistent with the description as a whole.

I claim:

1. A system for the automated dilution and delivery of a plurality of mixtures of diluent and liquid samples respectively disposed in an equal plurality of congruent sample containers to a particle counter, said congruent sample containers having an upwardly facing open mouth, the system comprising:

a) a container positioning member for receiving and retaining said congruent sample containers in an array with a respective unknown volume of liquid sample having been poured into each said sample container, wherein said unknown volume of each liquid sample is less than a pre-determined threshold volume that is less than the total volume of the respective sample container;

b) an automated diluent pumping mechanism having a diluent ingress port in fluid communication with a diluent source and a diluent egress port positionable in programmed sequence over the open mouth of each of said congruent sample containers retained in said array, for drawing a respective volume of a suitable diluent from said diluent source and for introducing said drawn volume of said diluent though said open mouth of each said sample container for mixing with the respective unknown volume of said liquid sample within each said sample container to together form a mixture of said liquid sample and said diluent, wherein the volume of said mixture is substantially equal to said pre-determined threshold volume;

(c) a mixer for agitating said mixture of liquid sample and diluent in said sample containers; and, (d) an automated mixture pumping mechanism having a mixture ingress port positionable in said programmed sequence over the mouth of each of said congruent sample containers retained in said array so as to be in fluid communication with said mixture of liquid sample and diluent in each said sample container, and a mixture egress port in fluid communication with said particle counter, for sequentially drawing a respective volume of mixture of liquid sample and diluent from said sample containers and for delivering the respective drawn volume of mixture of said liquid sample and said diluent to said particle counter.

2. The system of claim 1, further comprising an ultrasonic measuring device having an ultrasonic transducer and an ultrasonic sensor, for measuring the vertical position of the top surface of the liquid sample in each selected sample container with respect to said ultrasonic measuring device.

3. The system of claim 2, further comprising a computer/CPU that is connected in data communicating relation to said ultrasonic measuring device and that is programmed to calculate an accurate height measurement of the top surface of the liquid sample in the selected sample container with respect to an upwardly directed planar reference surface, using the measurement of the vertical position of the top surface of the liquid sample.

4. The system of claim 3, wherein said accurate height measurement of the top surface of the liquid sample in the selected sample container with respect to an upwardly directed planar reference surface is calculated by means of determining the vertical difference between the vertical position of the top surface of the liquid sample and the vertical position of said upwardly directed planar reference surface.

5. The system of claim 4, wherein said computer/CPU is programmed to calculate the volume of the liquid sample in said selected sample container based on said accurate height measurement combined with the known geometry of said congruent sample containers.

6. The system of claim 5, wherein said computer/CPU is further programmed to calculate the volume of diluent to add into said selected sample container necessary to obtain said pre-determined threshold volume of said mixture, based on the difference between the volume of said liquid sample in said selected sample container and said pre-determined threshold volume.

7. The system of claim 6, wherein said computer/CPU is further programmed to calculate the volume of diluent to add into said selected sample container to obtain said pre-determined threshold volume of said mixture, based on the viscosity of said liquid sample.

8. The system of claim 4, wherein said computer/CPU is programmed to calculate the volume of said liquid sample in said selected sample container based on a calibration graph of sample height versus sample volume.

9. The system of claim 3, wherein said computer/CPU is further programmed such that the pre-determined threshold volume of said mixture is the same volume for each sample container.

10. The system of claim 1, wherein said diluent pumping mechanism comprises a diluent syringe having a mouth, and a valve having a valve inlet in fluid communication with said diluent ingress port, a valve outlet in fluid communication with said diluent egress port, and a syringe opening connecting said valve inlet, said valve outlet, and the mouth of said diluent syringe in fluid communication with each other.

11. The system of claim 1, wherein said mixture pumping mechanism comprises a mixture syringe having a mouth, and a valve having a valve inlet in fluid communication with said mixture ingress port, a valve outlet in fluid communication with said mixture egress port, and a syringe opening connecting said valve inlet, said valve outlet, and the mouth of said mixture syringe in fluid communication with each other.

12. The system of claim 1, further comprising a horizontally oriented "X-Y" reference frame for operatively mounting said diluent egress port, said mixture ingress port and said mixer in horizontally movable relation for controlled two-dimensional movement in a horizontal "X-Y" coordinate grid, over said container positioning member.

13. The system of claim 12, wherein said horizontally oriented "X-Y" reference frame comprises a first horizontal track and a second horizontal track oriented substantially perpendicularly one to the other.

14. The system of claim 13, wherein said diluent ingress port, said diluent egress port and said mixer are mounted on a sampling head.

15. The system of claim 14, wherein said sampling head is mounted in vertically movable relation on said horizontally oriented "X-Y" reference frame by means of a mounting mechanism.

16. The system of claim 15, wherein said mounting mechanism is mounted in horizontally movable relation on said horizontally oriented "X-Y" reference frame.

17. The system of claim 16, wherein said mounting mechanism is mounted in horizontally movable relation in a "Y"-direction on said first horizontal track.

18. The system of claim 17, wherein said first horizontal track is mounted on said second horizontal track in horizontally movable relation in an "X"-direction that is perpendicular to said "Y"-direction.

19. The system of claim 18, further comprising an "X"-horizontal-movement motor for moving said first horizontal track in horizontally movable relation in said "X"-direction along said second horizontal track.

20. The system of claim 19, further comprising a "Y"-horizontal-movement motor for moving said mounting mechanism in horizontally movable relation in said "Y"-direction along said first horizontal track.

21. The system of claim 20, further comprising a "Z"-vertical-movement motor for moving said sampling head in vertically movable relation in said "Z"-direction along said mounting mechanism.

22. The system of claim 14, further comprising a delivery and uptake tube apparatus, and wherein said diluent ingress port and said diluent egress port are part of said delivery and uptake tube apparatus.

23. The system of claim 22, wherein said delivery and uptake tube apparatus is mounted on said sampling head.

24. The system of claim 1, wherein said unknown volume of each liquid sample is approximated with respect to indicia marked on each of said sample containers.

25. The system of claim 1, wherein said array is an ordered quadrilateral array.

26. A method of automatically diluting and delivering a plurality of mixtures of diluent and liquid samples respectively disposed in an equal plurality of congruent sample containers to a particle counter, said congruent sample containers having an upwardly facing open mouth, the method comprising the steps of:
   (a) receiving and retaining a plurality of congruent sample containers in an array in a container positioning member on a upwardly directed planar reference surface;
   ($b_1$) pouring an unknown volume of said liquid sample into each said sample container, wherein said unknown volume of each liquid sample is less than a pre-determined threshold volume that is less than the total volume of the respective sample container;
   ($b_2$) mechanically moving a measurement device into place over said unknown volume of liquid in said selected sample container;
   ($b_3$) electronically measuring the vertical position of the top surface of the liquid sample in each selected sample container with respect to said measurement device;
   (c) drawing a respective volume of a suitable diluent from a diluent source;
   (d) introducing said drawn volume of said diluent though said open mouth of each said sample container for mixing with the respective unknown volume of said liquid sample within each said sample container to together form a mixture of said liquid sample and diluent, wherein the volume of said mixture is substantially equal to said pre-determined threshold volume;
   (e) agitating said mixture of liquid sample and diluent in said sample containers;
   (f) sequentially drawing a respective volume of mixture of liquid sample and diluent from said sample containers; and
   (g) delivering the respective drawn volume of mixture of said liquid sample and said diluent to said particle counter.

27. The method of claim 26, further comprising the step of, after step ($b_3$) and before step (c):
   ($b_4$) electronically calculating an accurate height measurement of the top surface of said liquid sample in said selected sample container with respect to said upwardly directed planar reference surface, using the measurement of the vertical position of the top surface of the liquid sample.

28. The method of claim 27, wherein said accurate height measurement of the top surface of the liquid sample in the selected sample container with respect to an upwardly directed planar reference surface is calculated by means of determining the vertical difference between the vertical position of the top surface of the liquid sample and the vertical position of said upwardly directed planar reference surface.

29. The method of claim 27, further comprising the step of, after step ($b_4$) and before step (c):
   ($b_5$) electronically calculating the volume of said unknown volume of liquid in said selected sample container, using the accurate height measurement calculated in step ($b_4$) combined with the known geometry of said congruent sample containers.

30. The method of claim 29, further comprising the step of, after step ($b_5$) and before step (c):
   ($b_6$) electronically calculating the volume of diluent to add into said selected sample container necessary to obtain said pre-determined threshold volume of said mixture, based on the difference between the volume of said liquid sample in said selected sample container and said pre-determined threshold volume.

31. The method of claim 30, wherein step ($b_6$) electronically determining the volume of diluent to add into said selected sample container, is based on the viscosity of said liquid sample.

32. The method of claim 29, wherein the volume of said unknown volume of liquid in said selected sample container is calculated based on a calibration graph of sample height versus sample volume.

33. The method of claim 31, further comprising the step of, step ($b_6$) and before step (c):
   ($b_7$) determining a dilution ratio of said unknown volume of liquid and said diluent in said sample container, and performing step (c) if the dilution ratio of the unknown volume of liquid to the diluent is between about 1:0 and 1:9.

34. The method of claim 26, wherein said pre-determined threshold volume is the same volume for each sample container.

35. The method of claim 26, wherein said unknown volume of each liquid sample is approximated with respect to indicia marked on each of said sample containers.

36. The method of claim 26, wherein said array is an ordered quadrilateral array.

* * * * *